(12) United States Patent
Svensson et al.

(10) Patent No.: US 7,826,593 B2
(45) Date of Patent: Nov. 2, 2010

(54) COLLIMATOR

(75) Inventors: Roger Svensson, Värmdö (SE); Anders Brahme, Danderyd (SE)

(73) Assignee: C-Rad Innovation AB, Uppsala (SE)

( * ) Notice: Subject to any disclaimer, the term of this patent is extended or adjusted under 35 U.S.C. 154(b) by 0 days.

(21) Appl. No.: 12/519,565

(22) PCT Filed: Dec. 7, 2007

(86) PCT No.: PCT/SE2007/001090
§ 371 (c)(1),
(2), (4) Date: Aug. 10, 2009

(87) PCT Pub. No.: WO2008/076035
PCT Pub. Date: Jun. 26, 2008

(65) Prior Publication Data
US 2010/0034357 A1 Feb. 11, 2010

Related U.S. Application Data

(60) Provisional application No. 60/875,535, filed on Dec. 19, 2006.

(51) Int. Cl.
*A61N 5/10* (2006.01)
(52) U.S. Cl. .......................... 378/65; 378/152
(58) Field of Classification Search .................. 378/65, 378/145, 146, 147–153
See application file for complete search history.

(56) References Cited

U.S. PATENT DOCUMENTS 6,730,924 B1 5/2004 Pastyr
2004/0213381 A1* 10/2004 Harada ........................ 378/152

FOREIGN PATENT DOCUMENTS

GB 2403884 1/2005
WO 03079373 9/2003

OTHER PUBLICATIONS

International Search Report dated Apr. 17, 2008.

\* cited by examiner

*Primary Examiner*—Hoon Song
(74) *Attorney, Agent, or Firm*—Young & Thompson

(57) ABSTRACT

A collimator (1) primarily adapted for usage in a narrow scanned pencil beam radiation therapy system (100) includes adjacent pairs (5) of collimator leaves (10, 20). An inner portion (12) of a collimator leaf (10) facing the opposite leaf (20) of a pair (5) is made of a first material having high linear radiation attenuation. The remaining, major portion (14) of the leaf (10) is made of a second material having a comparatively low density, weight and radiation attenuation. The collimator (1) provides effective penumbra trimming of a radiation beam (60), while simultaneously protecting healthy tissue around a tumor in an irradiated patient (80) from the radiation. The new design results in a significantly more compact, lighter and less expensive collimator (1) as compared to traditional collimators.

16 Claims, 13 Drawing Sheets

COLLIMATOR

TECHNICAL FIELD

The present invention generally relates to a collimator, and in particular to a penumbra-trimming collimator useful in connection with scanning beam therapy and beam collimation.

BACKGROUND

Approximately half of the current young generation in the Western world will at some point in their lives be diagnosed as having cancer and this frequency is slowly increasing. More than half of these patients are likely to receive radiation therapy, due in particular to the increasing use and efficacy of intensity modulated radiation therapy (IMRT). Both the rising costs for cancer care and the adverse side-effects in normal tissues call for more locally effective treatment procedures such as radiation therapy, which is undoubtedly more cost-effective and generally more curative than both surgery or chemotherapy, and is being recommended more and more extensively. Extensive and mutilating surgery is now often replaced by minimally invasive surgery and will in the future be superseded by highly precise intensity modulated photon and light ion radiation therapy.

Improvements in tumor diagnostics, including four-dimensional computed tomography (4D-CT), magnetic resonance imaging (MRI) and the combination of positron emission tomography (PET) with CT (4D-PET-CT), both enhance our knowledge about tumor spread in relation to normal tissues and allow more precise delivery of radiation, thereby optimizing the treatment at a reasonable cost.

Furthermore, intensity modulated radiation therapy is rapidly becoming the treatment of choice for most tumors with respect to minimizing damage to the normal tissues and maximizing tumor control. Today, intensity modulated beams are most commonly delivered using segmental multileaf collimation, although an increasing number of radiation therapy departments are employing dynamic multileaf collimation. The irradiation time using dynamic multileaf collimation depends strongly on the nature of the desired dose distribution, and it is difficult to reduce this time to less than the sum of the irradiation times for all individual peaks heights using dynamic leaf collimation. Therefore, the intensity modulation will considerably increase the total treatment time.

Document [1] discloses a collimator arrangement consisting of a primary collimator, a multileaf collimator and two pairs of independently adjustable block diaphragm leaves at right angles to each other. By using rectilinear displacement of the multileaf collimator leaves and the block diaphragm leaves, a compact arrangement can be provided which fits into a standard collimator head. The diaphragm leaves can, in order to reduce the cost, have a respective inner portion made of tungsten while the remainder of the leaves is made of lead.

SUMMARY

The present invention overcomes these and other drawbacks of the prior art arrangements.

It is a general object of the present invention to provide a light, compact and inexpensive collimator design.

It is a particular object of the invention to provide a collimator suitable for usage in connection with a narrow pencil beam scanning radiation gantry.

These and other objects are met by the invention as defined by the accompanying patent claims.

Briefly, the present invention involves a collimator comprising at least one pair of collimator leaves. Each leaf comprises an inner high-attenuating penumbra-trimming portion and a remaining low-attenuating support portion. The penumbra-trimming portion constitutes the leaf portion in connection with the leaf end facing the opposite collimator leaf of the leaf pair. The support portion is then the major leaf portion facing away from the opposite leaf of the leaf pair.

According to the invention, a provided radiation beam, such as a photon, electron or light ion beam, preferably a narrow scanned pencil beam, will substantially only incident on the penumbra-trimming leaf portion. As a consequence, the material of this inner portion has a high linear radiation attenuation capability radiation, which is larger than the corresponding linear attenuation capability of the support portion.

The penumbra-trimming portion is made of a first metal or a first alloy of the first metal. The first metal has very high linear radiation attenuation coefficient, preferably such a coefficient of at least 1 $cm^{-1}$ for photon energies of at least 50 MV. The first metal is selected from high atomic number metals having this high linear attenuation coefficient, such as tungsten, osmium and iridium.

The support portion is correspondingly made of a second metal or a second alloy of the second metal. This metal material does not have the stringent demands on high linear radiation attenuation coefficient as the first metal (alloy) material. As a consequence, the linear radiation attenuation coefficient of this material is lower than the corresponding linear attenuation coefficient of the first metal (alloy). The second metal is selected from metals and metal alloys having correspondingly lower atomic number as compared to the first metal, such as iron, aluminium and steel.

Preferred materials of the penumbra-trimming leaf portion includes high atomic number metals and metal alloys having a density of at least 15 $g/cm^3$. The material of the support portion does not have the same radiation attenuating demands and is therefore, for reducing the weight, size and cost of the collimator, preferably made of a light metal or metal alloy materials.

A cost-effective procedure for rapid intensity modulation is using the collimator of the present invention in connection with narrow scanned photon, electron and light ion beams. The collimator is then mainly employed for penumbra trimming but also for protecting the patient body from radiation outside of a treatment volume. With this approach, the irradiation time is largely independent of the complexity of the desired intensity distribution and, in case of photon beams, may even be shorter than with uniform beams. The intensity modulation is achieved primarily by scanning of a narrow elementary photon pencil beam generated by directing a narrow well focused high energy electron beam onto a thin bremsstrahlung target.

The fast low-weight collimator of the invention is capable of further sharpening the penumbra at the edge of the elementary scanned beam, in order to minimize the dose or radiation response of healthy tissues. In the case of photon beams, such a collimator can be placed relatively close to the bremsstrahlung target to minimize its size. It can also be flat and thin, e.g. only 15-25 mm thick in the direction of the beam with edges made of, for example, tungsten or preferably osmium to optimize the sharpening of the penumbra. The low height of the collimator will minimizes edge scatter from glancing incidence. The major portions of the collimator leafs can then be made of, for example, steel or even aluminum (or other light metals and alloys), so that the total weight of the collimator will be very low, such as about 10 kg, which may even allow high-speed collimation in real time in synchrony with organ movements.

The invention offers the following advantages:
The collimator is a perfect penumbra trimmer due to material selection;
The collimator can operate very fast;
The collimator is of light weight;
The collimator can be manufactured at a low cost compared to the prior art collimators;
The collimator can easily be operated in due to low power needs; and
The collimator can be used in connection with all radiation particle types employed in radiation diagnosis and/or treatment.

Other advantages offered by the present invention will be appreciated upon reading of the below description of the embodiments of the invention.

SHORT DESCRIPTION OF THE DRAWINGS

The invention together with further objects and advantages thereof, may best be understood by making reference to the following description taken together with the accompanying drawings, in which.

Figures 6, 7A:
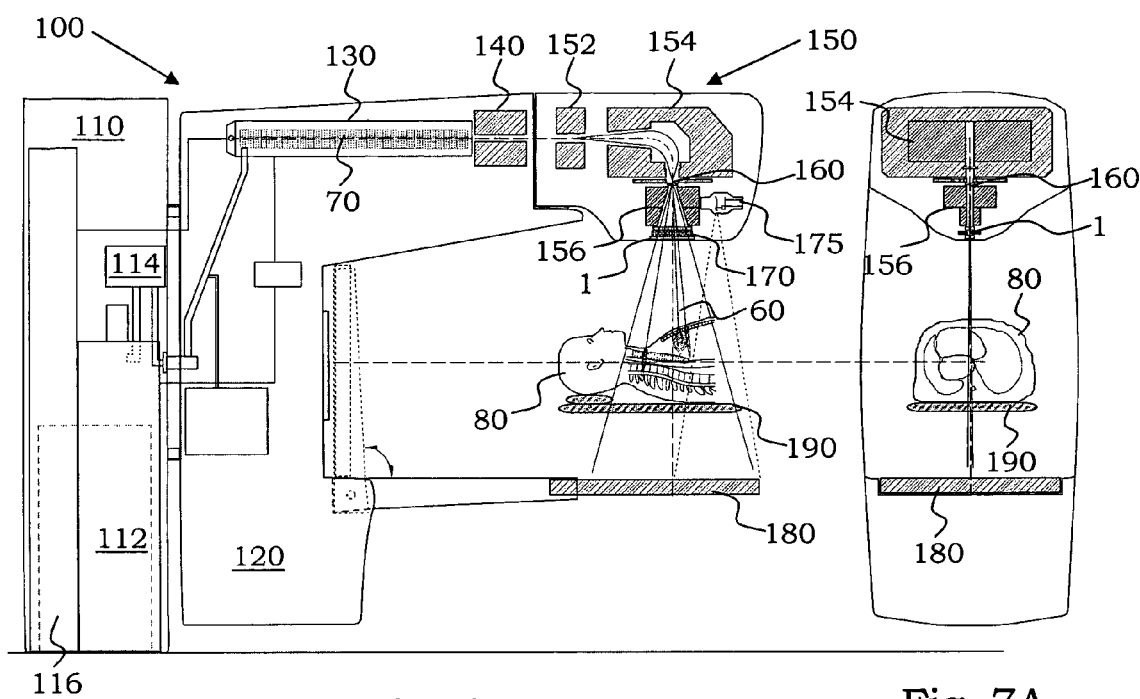
FIG. 6 is a schematic overview of a radiation system in which a multileaf collimator of the present invention can be arranged.
Figures 7B, 7C, 7D:
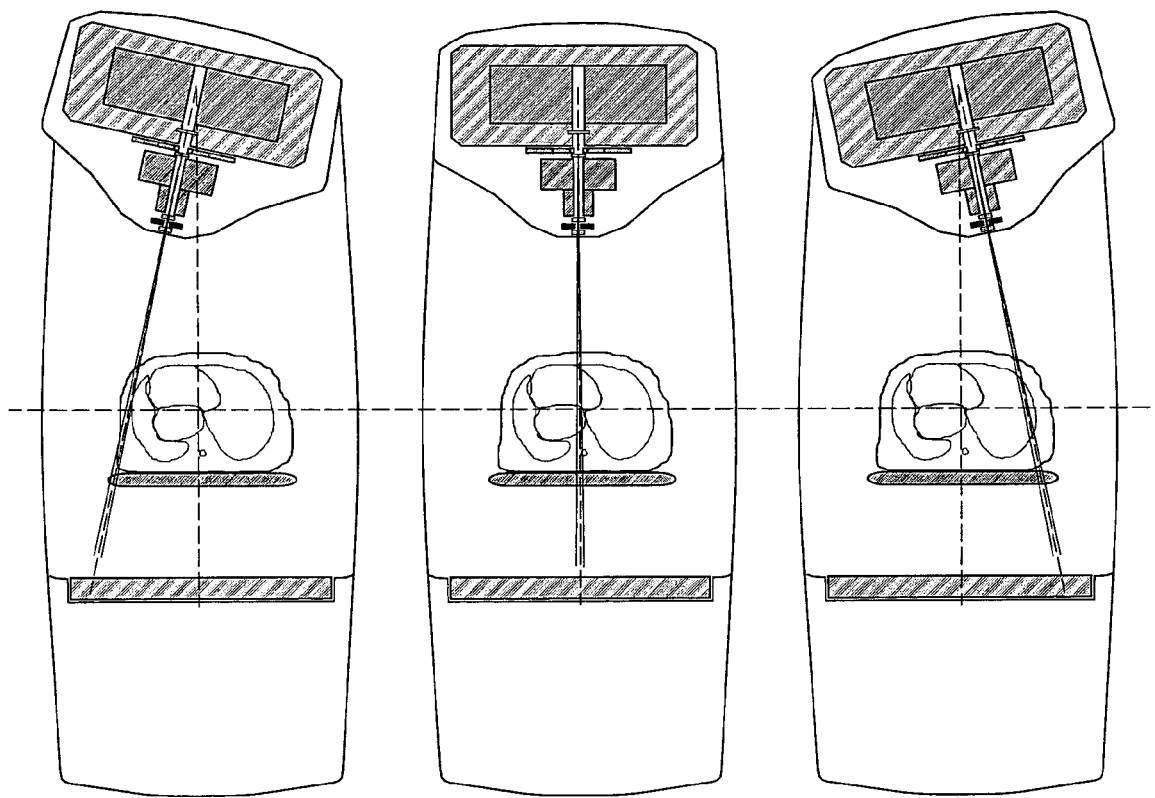
Figures 7E, 7F:
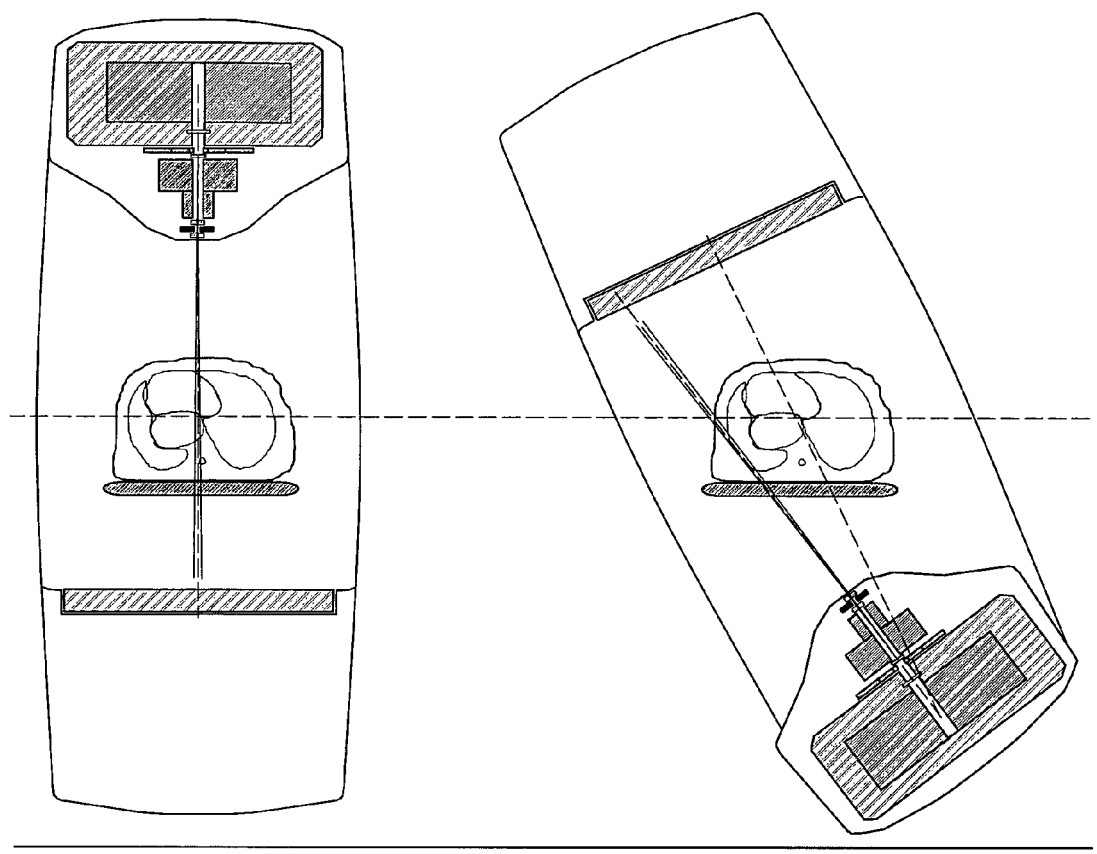

FIGS. 7A to 7F schematically illustrate operation of the radiation system of FIG. 6 through narrow beam scanning from different incident angles.

Figure 8:
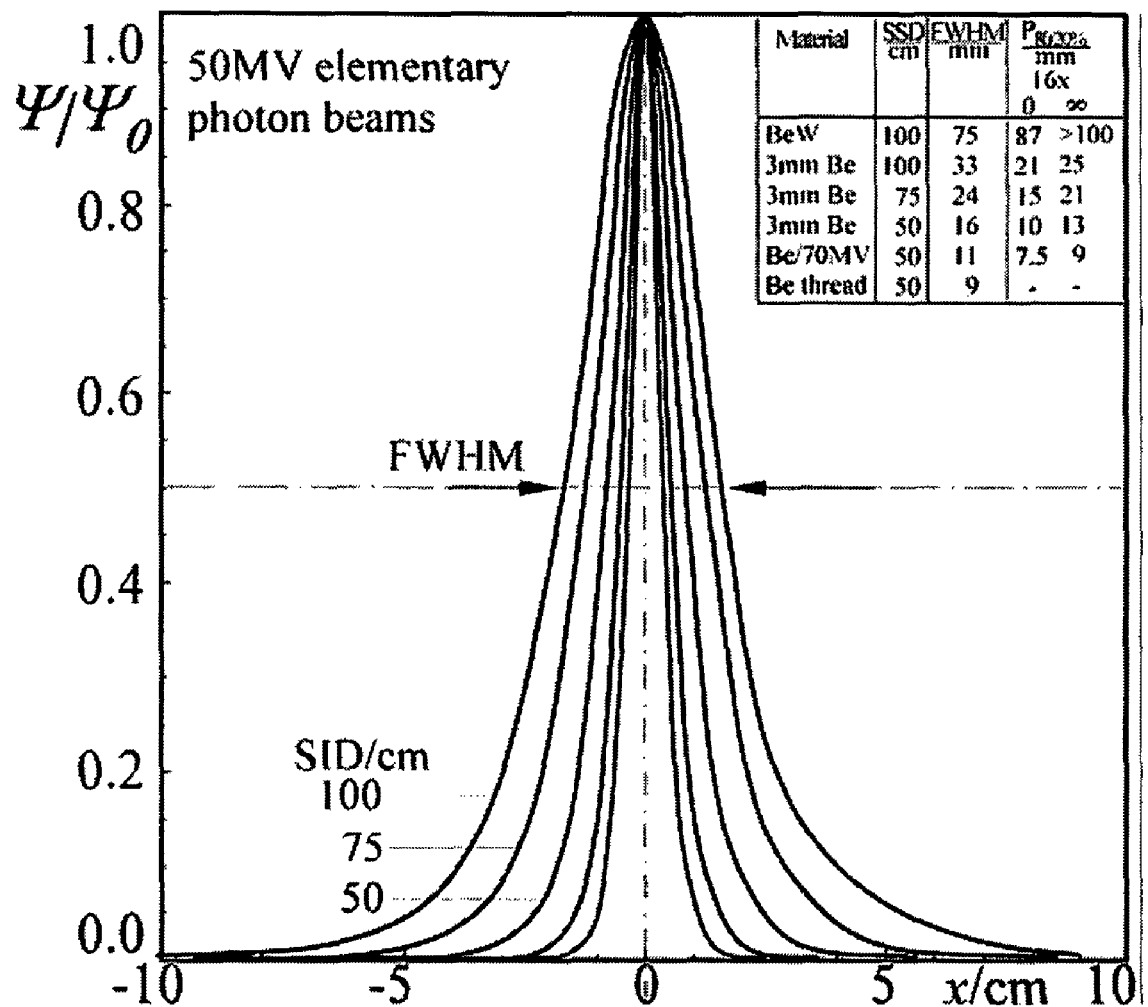
Figure 9:
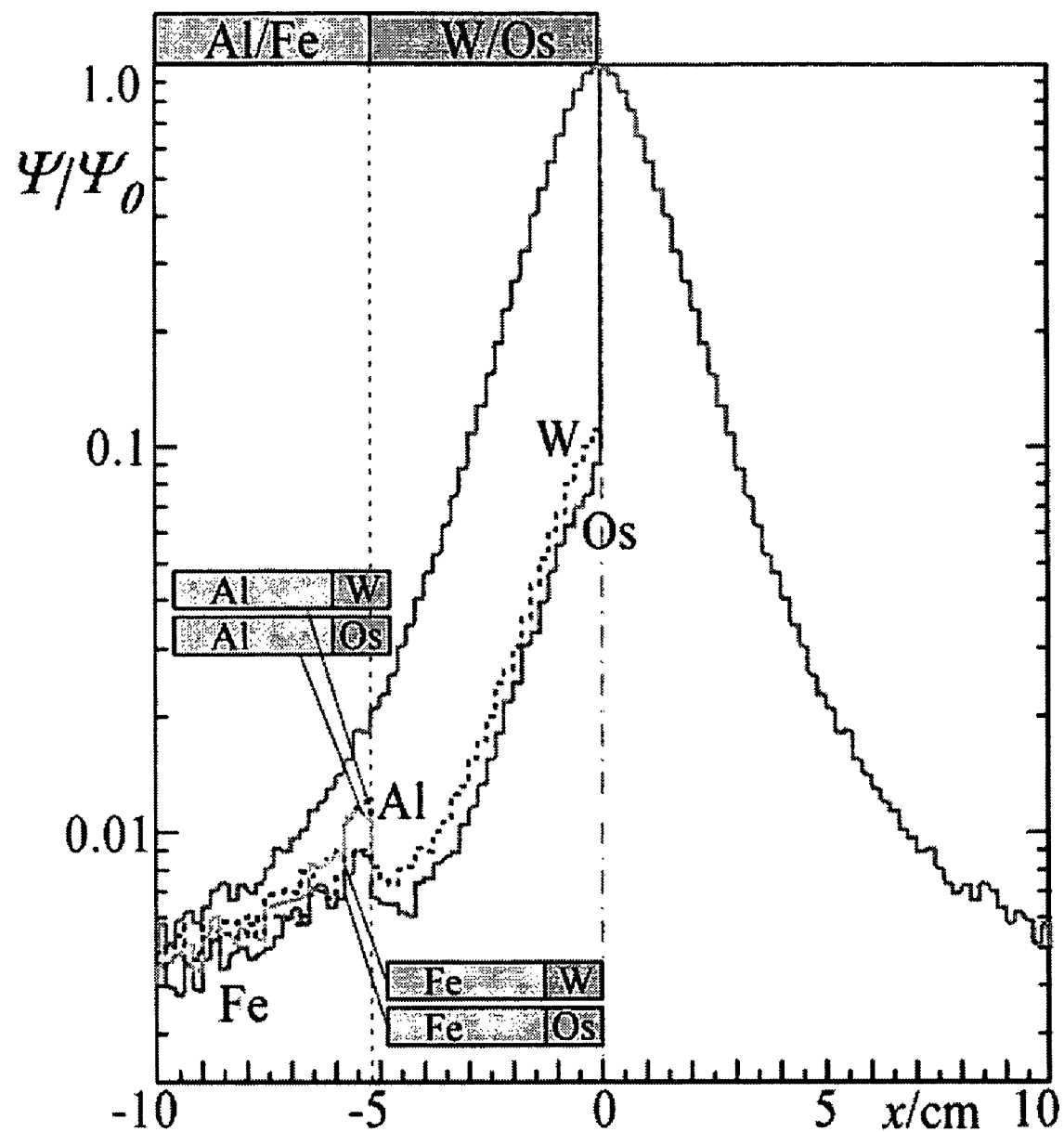
Figure 10:
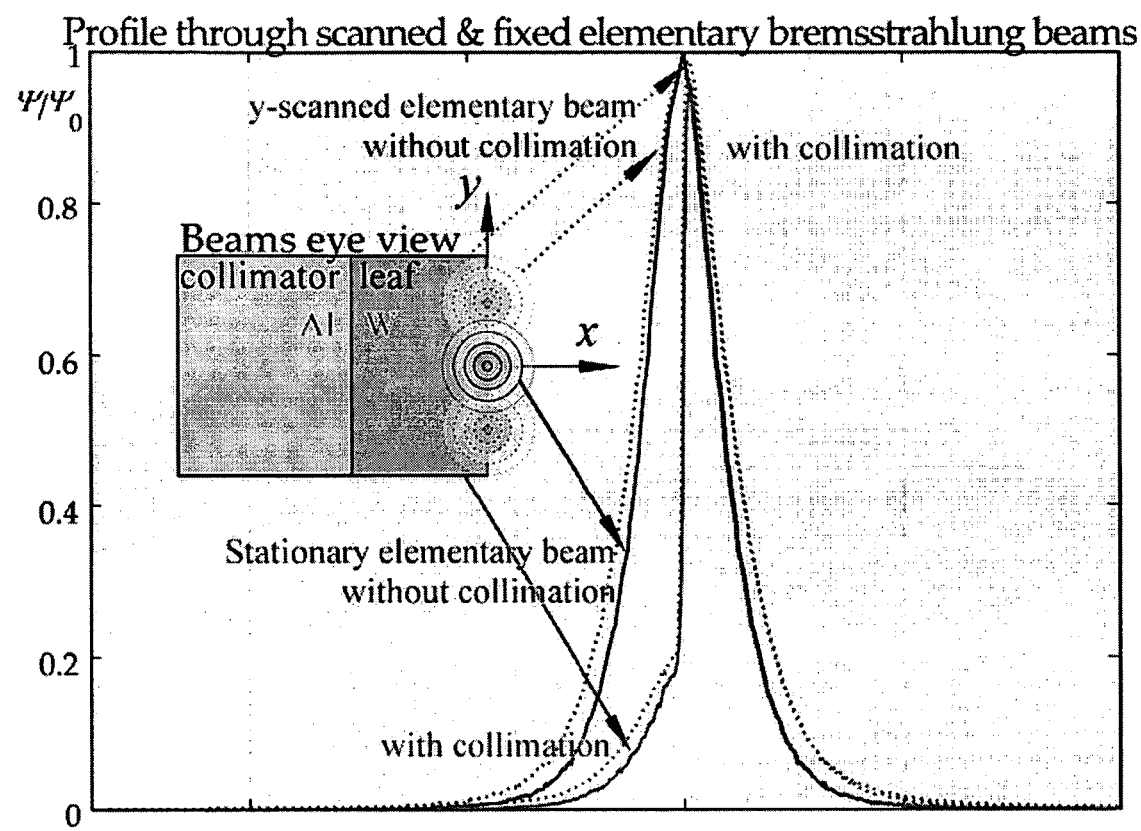
Figure 11:
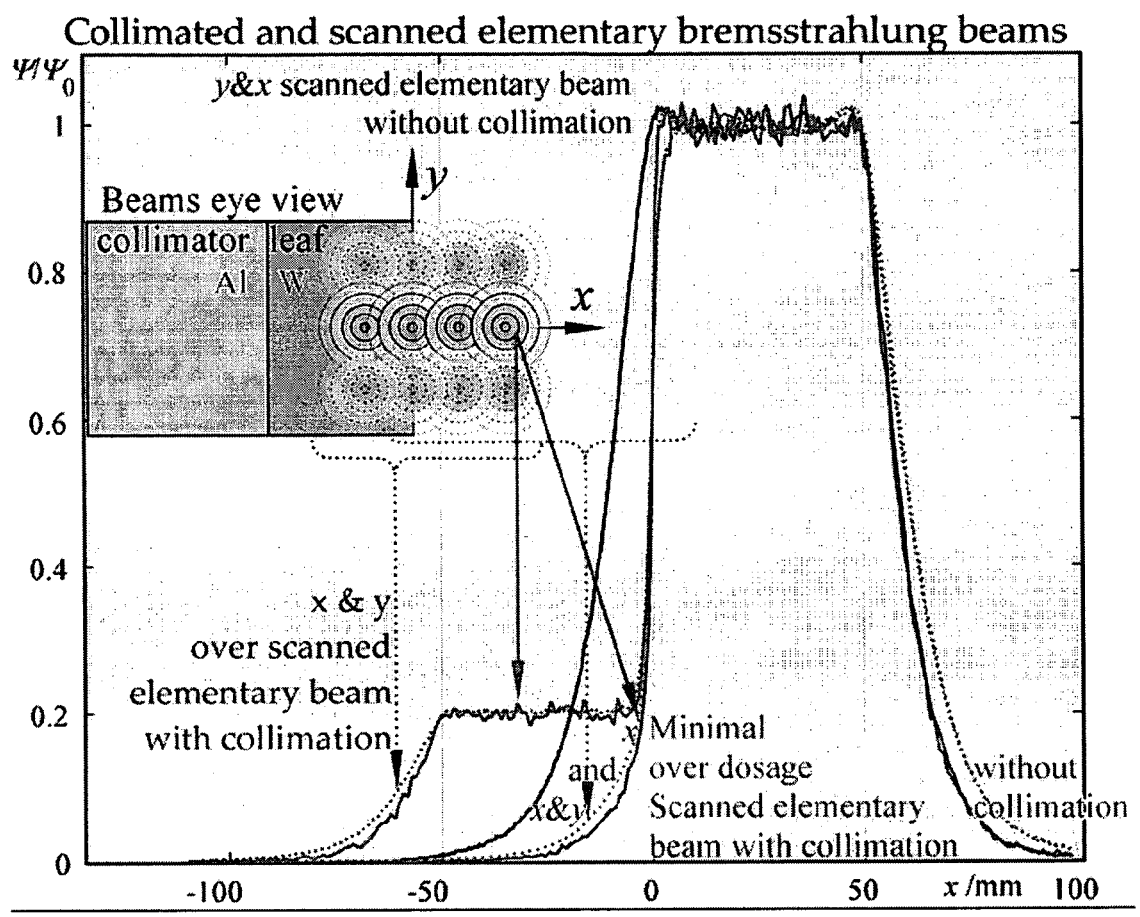
Figure 12:
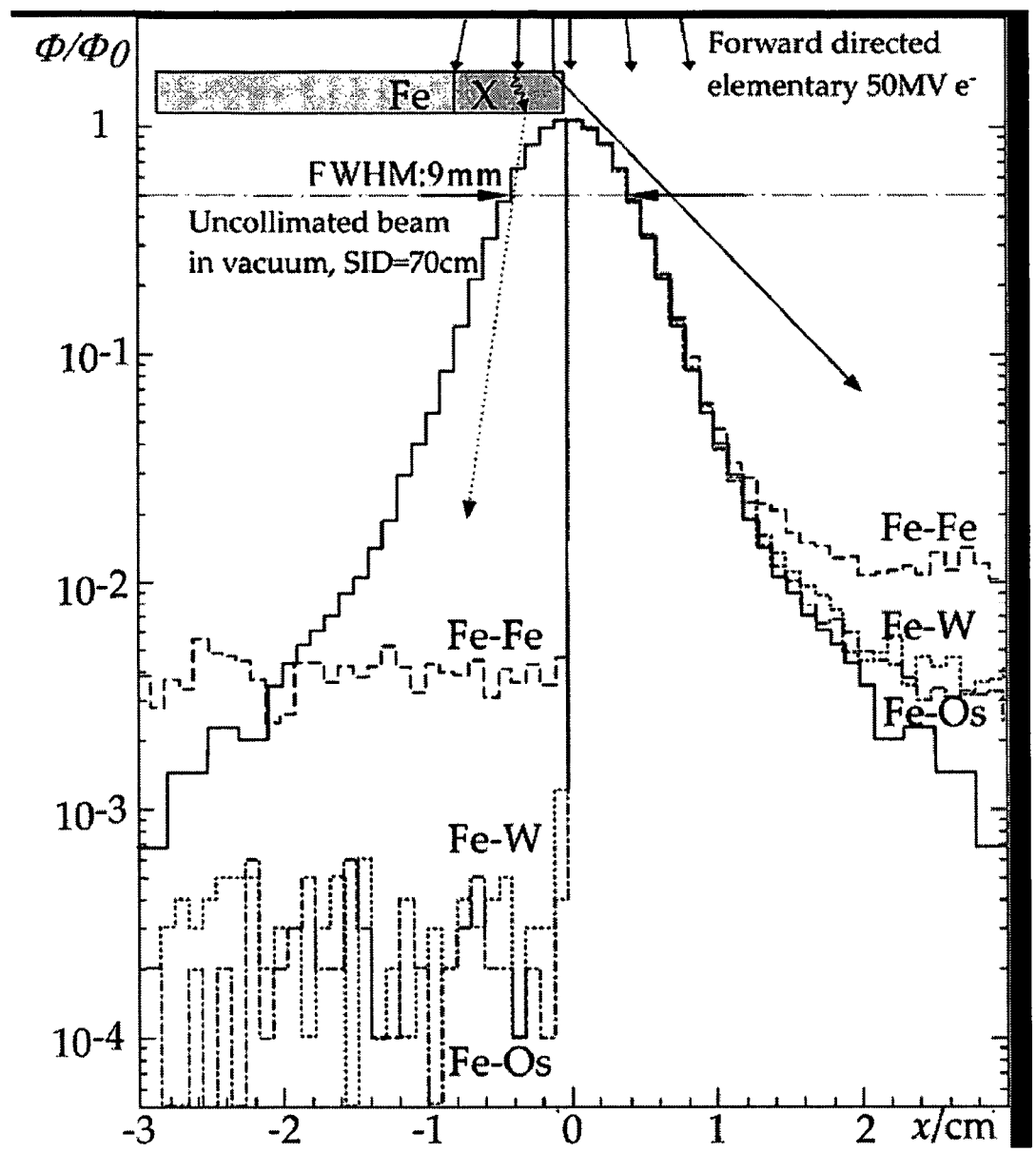
Figure 13:
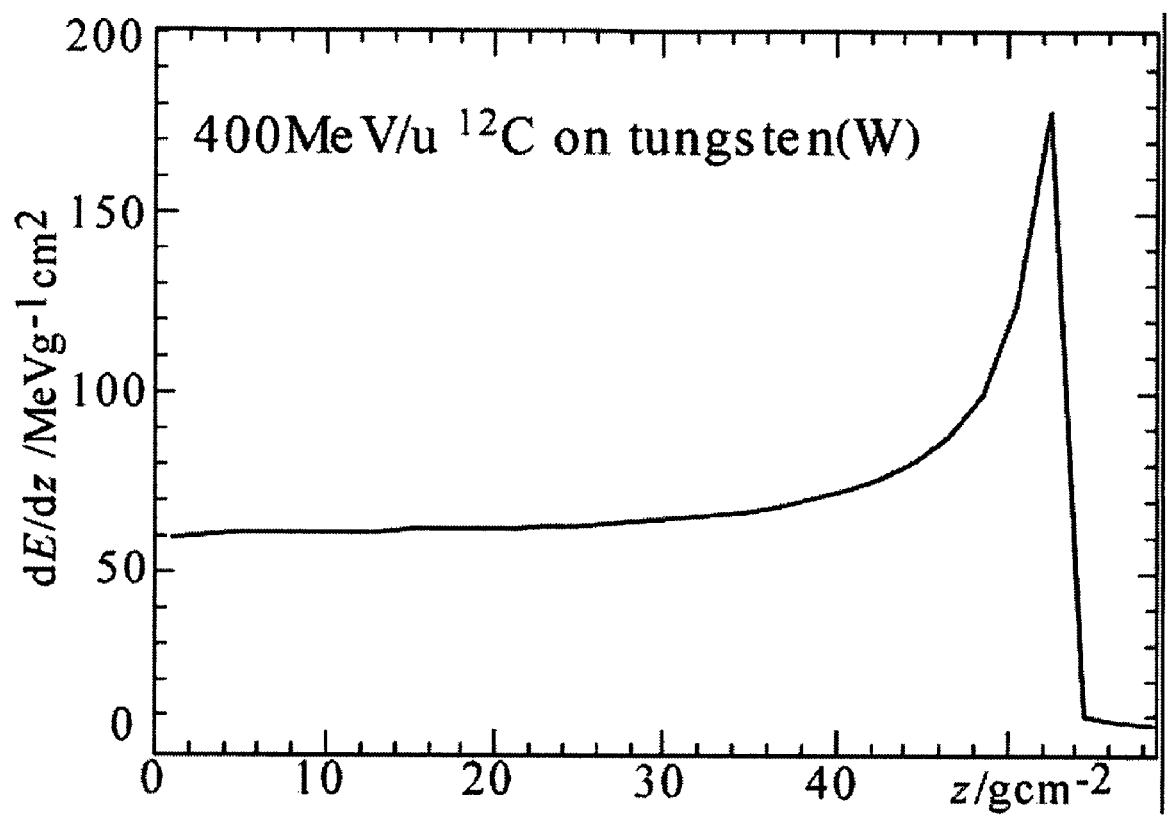
Figure 14:
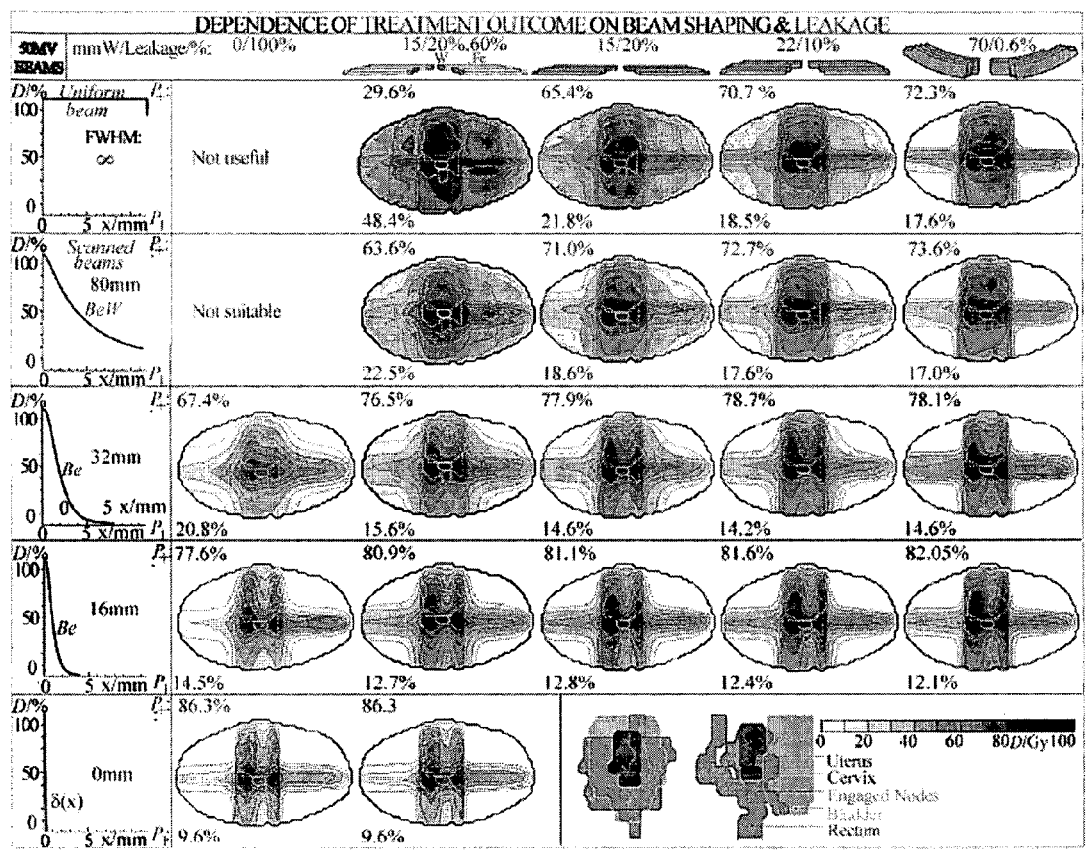
Figure 15:
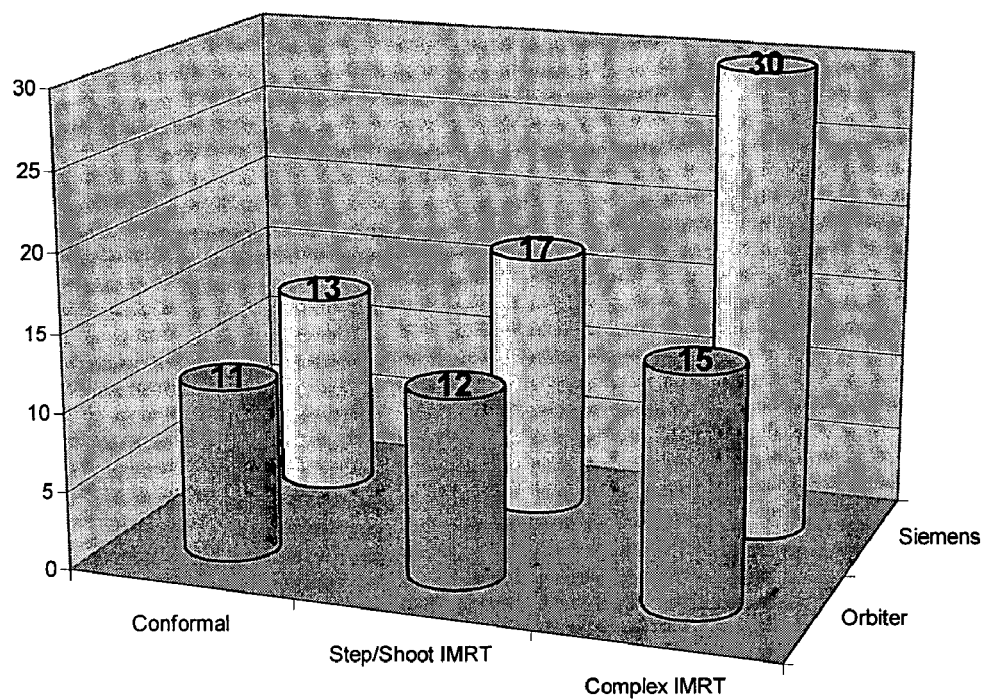
Figure 16:
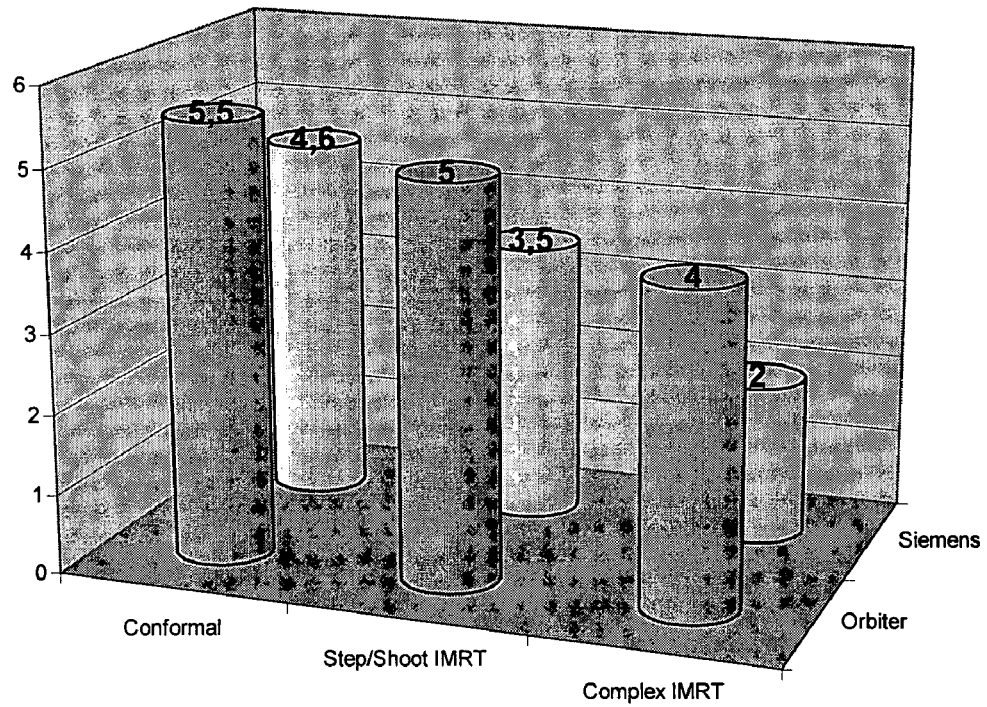

FIG. 8 illustrates dose distributions of elementary 50 MV bremsstrahlung beams for different target designs that can be used according to the present invention;

FIG. 9 illustrates Monte-Carlo calculations of the transmission of forward directed bremsstrahlung through different embodiments of a multileaf collimator according to the present invention;

FIG. 10 discloses profiles of scanned and stationary photon beams combined with collimation with a multileaf collimator according to the present invention;

FIG. 11 illustrates characteristics of collimated and scanned elementary photon beams in combination with a multileaf collimator according to the present invention;

FIG. 12 illustrates the significance of employing a high density edge to minimize the collimator electron in-scatter in connection with electron therapy;

FIG. 13 is the Bragg curve for a typical broad therapeutic carbon beam with energy of 400 MeV/u impinging on a tungsten collimator 30 mm in thickness;

FIG. 14 illustrates optimization of the outcome of treatment with primary beams of varying quality utilizing uniform and scanned beam delivery and simultaneous optimization with a single multileaf setting for collimators of different thicknesses and edges as well as without collimation;

FIG. 15 illustrates a comparison of treatment time for different radiation therapy systems; and FIG. 16 illustrates a comparison of patient throughput for different radiation therapy systems.

DETAILED DESCRIPTION

Throughout the drawings, the same reference characters will be used for corresponding or similar elements.

The present invention generally relates to a novel design of a collimator having significantly reduced weight, cost and overall size as compared to previously employed collimators. The collimator of the present invention is in particular adapted for usage in a radiation gantry using narrow scanned radiation beams, often denoted a pencil-beam scanning system in the art.

The collimator of the invention comprises at least one pair of collimator leaf. In most preferred embodiments, the collimator comprises multiple adjacent leaves and is therefore a so-called multileaf collimator. In the following, the collimator of the invention is mainly described embodied as a multileaf collimator unless mentioned otherwise. The invention, though, also encompasses single-pair collimators that comprise one pair of two opposite collimator leaves.

Figure 1:
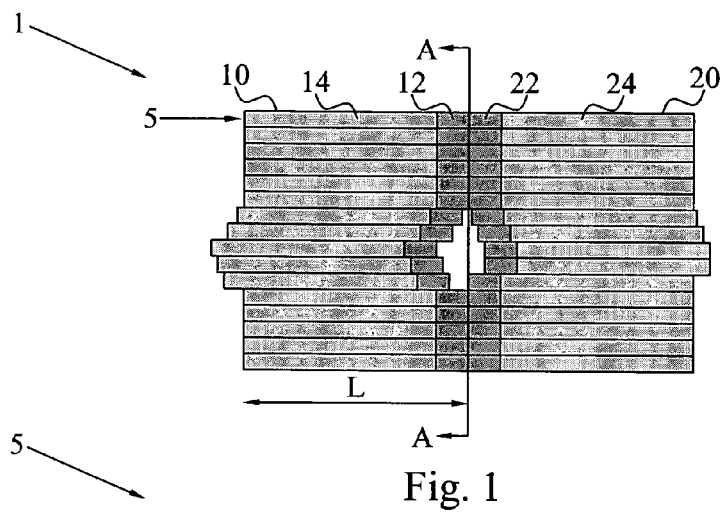
FIG. 1 is a schematic overview of a multileaf collimator of the present invention seen from a top view.

FIG. 1 is a schematic overview of a multileaf collimator 1 according to an embodiment of the present invention seen from a top view. The collimator 1 comprises multiple, i.e. at least two but typically about 10-100, adjacent pairs 5 of collimator leaves 10, 20. In clear contrast to the prior art, a collimator leaf 10, 20 of the invention comprises an inner penumbra-trimming portion 12, 22 made of a first metal material and an outer or remaining support portion 14, 24 made of a second different metal material. The inner leaf portion 12 constitutes the end portion of the leaf 10 facing the opposite collimator leaf 20 of the leaf pair 5. Thus, traveling from one end of the collimator 1 through a leaf pair 5 (such as from the left to the right in FIG. 2), one first encounters the support leaf portion 14 made of the second material of the first collimator leaf 10 and then, as one comes closer to the opposite end of the first collimator leaf 10, enters the trimming leaf portion 12 made of the first material. Thereafter, one enters the trimming portion 22 of the second collimator leaf 20, which is also made of the first material and then leaves this inner portion 22 and enters the support portion 24 of the second material for the second collimator leaf 20.

As is illustrated in FIG. 1, preferably all collimator leaves 10, 20 of the collimator 1 contains a respective inner portion 12, 22 of a first material and a respective remaining portion 14, 24 of a second material.

The characterizing feature of the collimator leaves 10, 20 of the present invention is that the first material is a first metal material or a first alloy material of the first metal and has a first high linear attenuation capability or coefficient ($\mu_1$) [cm$^{-1}$]. This material will perform the penumbra trimming and collimating function of the collimator. As a consequence, the material therefore preferably has very high linear attenuation coefficient to be as thin as possible to thereby get a sharp penumbra trimming. The trimming portion preferably has attenuation coefficient and thickness selected so that it attenuates at least 70%, preferably at least 75%, more preferably around at least 80% of the incident radiation hitting the trimming leaf portion. As a consequence, the radiation leakage is preferably no more than 20% from this portion.

As the radiation beam will primarily only incident on the trimming portion and not the support portion, the second material of the support portion does not have the stringent radiation attenuation demands as the first materials. In clear contrast, the material selection is mainly a demand for low cost, low density and light weight. As a consequence, the second material is a second metal material or a second alloy material of the second metal. The second material has lower linear attenuation coefficient ($\mu_2$) [cm$^{-1}$] than the first material, i.e. $\mu_1 > \mu_2$. Preferably, the linear attenuation coefficient of the second material is lower than 50% of the linear attenuation coefficient of the first material and even lower than 25% for the first material and still the collimator of the invention will operate excellently.

Furthermore, the first material preferably has a high radiation mass attenuation capability or coefficient ($\mu_1/\rho_1$) [cm$^2$/g] and the second material has a second radiation mass attenuation capability or coefficient ($\mu_2/\rho_2$) [cm$^2$/g] that is lower than the first radiation attenuating capability, i.e. $\mu_2/\rho_2 < \mu_1/\rho_1$.

For a narrow beam of mono-energetic photons, the change in radiation beam intensity at some distance in a material can be expressed in the form of the equation 1:

$$dI(x) = -I(x) \times n \times \sigma \times dx \quad (1)$$

where dI(x) is the change in intensity, I is the initial intensity, n is the number of atoms/cm$^3$, $\sigma$ is a proportionality constant that reflects the total probability of a photon being scattered or absorbed and dx is the incremental thickness of material traversed. Integrating the equation and substituting n×σ with the linear attenuation coefficient $\mu$ gives the expression:

$$I = I_0 e^{-\mu x} \quad (2)$$

where I is the intensity of photons transmitted across some distance x, $I_0$ is the initial intensity of photons, $\mu$ is the linear attenuation coefficient according to above and x is the distance traveled.

The linear attenuation coefficient ($\mu$) [cm$^{-1}$] describes the fraction of a radiation beam that is absorbed or scattered per unit thickness of the absorber. This value is of key importance for beam collimation and basically accounts for the number of atoms in a cubic cm volume of material and the probability of a photon being scattered or absorbed from the nucleus or an electron of one of these atoms. Table I lists linear attenuation coefficients for different materials at different monoenergetic photon beams.

TABLE I linear attenuation coefficients ($\mu$)

| Photon energy (MeV) | Linear attenuation coefficient (cm$^{-1}$) | | | | | |
|---|---|---|---|---|---|---|
| | Tungsten | Osmium | Iridium | Lead | Iron | Aluminium |
| 1 | 1.28 | 1.52 | 1.52 | 0.80 | 0.47 | 0.17 |
| 1.25 | 1.08 | 1.27 | 1.28 | 0.66 | 0.42 | 0.15 |
| 1.5 | 0.97 | 1.14 | 1.14 | 0.59 | 0.39 | 0.14 |
| 2 | 0.86 | 1.01 | 1.01 | 0.52 | 0.34 | 0.12 |
| 3 | 0.79 | 0.93 | 0.93 | 0.48 | 0.29 | 0.10 |
| 4 | 0.78 | 0.92 | 0.92 | 0.47 | 0.26 | 0.08 |
| 5 | 0.79 | 0.93 | 0.94 | 0.48 | 0.25 | 0.08 |
| 6 | 0.81 | 0.96 | 0.96 | 0.50 | 0.24 | 0.07 |
| 8 | 0.86 | 1.02 | 1.02 | 0.53 | 0.24 | 0.07 |
| 10 | 0.92 | 1.08 | 1.09 | 0.56 | 0.24 | 0.06 |
| 15 | 1.04 | 1.23 | 1.24 | 0.64 | 0.24 | 0.06 |
| 20 | 1.14 | 1.35 | 1.35 | 0.70 | 0.25 | 0.06 |
| 50$^\perp$ | 1.09 | 1.29 | 1.29 | 0.67 | 0.25* | 0.06 |
| 70$^\perp$ | 1.19 | 1.44 | 1.44 | 0.75 | 0.26* | 0.06 |

*Steel
$^\perp$MV instead of MeV

The quotation of the linear attenuations of the second material and the first material $$\left(\frac{\mu_2}{\mu_1}\right)$$

is preferably lower than 0.50, more preferably below 0.25, especially for radiation beam energy content of at least 1 MV, preferably at least 10 MV more preferably at least 20 MV such as 50 MV or 70 MV.

The mass attenuation coefficient can then be calculated as the linear attenuation divided by the density of the material:

$$\frac{\mu}{\rho} \quad (3)$$

By replacing x in equation 2 with x=y/ρ, where y is the mass thickness of the material [g/cm$^2$] and $\rho$ [g/cm$^3$] is the density of the material, the equation becomes:

$$I = I_0 e^{-\frac{\mu}{\rho} y} \quad (4)$$

Table II below lists mass attenuation coefficients for different materials at different monoenergetic photon beams.

TABLE II mass attenuation coefficients ($\mu/\rho$)

| Photon energy (MeV) | Mass attenuation coefficient (10$^{-2}$ cm$^2$/g) | | | | | |
|---|---|---|---|---|---|---|
| | Tungsten | Osmium | Iridium | Lead | Iron | Aluminium |
| 1 | 6.62 | 6.71 | 6.79 | 7.10 | 6.00 | 6.14 |
| 1.25 | 5.58 | 5.63 | 5.69 | 5.88 | 5.35 | 5.50 |
| 1.5 | 5.00 | 5.03 | 5.08 | 5.22 | 4.88 | 5.01 |
| 2 | 4.33 | 4.46 | 4.50 | 4.61 | 4.27 | 4.32 |
| 3 | 4.08 | 4.10 | 4.14 | 4.23 | 3.62 | 2.54 |
| 4 | 4.04 | 4.07 | 4.10 | 4.20 | 3.31 | 3.11 |
| 5 | 4.10 | 4.13 | 4.17 | 4.27 | 3.15 | 2.84 |
| 6 | 4.21 | 4.24 | 4.29 | 4.39 | 3.06 | 2.66 |
| 8 | 4.47 | 4.51 | 4.56 | 4.68 | 2.99 | 2.44 |
| 10 | 4.75 | 4.79 | 4.84 | 4.97 | 2.99 | 2.32 |
| 15 | 5.38 | 5.44 | 5.50 | 5.66 | 3.09 | 2.20 |
| 20 | 5.89 | 5.96 | 6.02 | 6.21 | 3.22 | 2.17 |
| 50$^\perp$ | 5.64 | 5.70 | 5.75 | 5.93 | 3.15* | 2.18 |
| 70$^\perp$ | 6.18 | 6.36 | 6.42 | 6.61 | 3.33* | 2.18 |

*Steel
$^\perp$MV instead of MeV

The first metal is a high atomic number metal, such as having an atomic number of at least 72 according to the periodic table of the elements. Preferred such high atomic number metals are the so-called heavy metals and heavy metal alloys, such as tungsten, osmium and iridium. In order to achieve the desired level of radiation attenuation, the first material preferably has a density of at least 15 g/cm$^3$, more preferably at least 17 g/cm$^3$, such as around or above 20 g/cm$^3$. Currently preferred high atomic number materials include tungsten (W, density about 19.25 g/cm$^3$), osmium (Os, density about 22.61 g/cm$^3$) and iridium (Ir, density about 22.42 g/cm$^3$) and different alloys thereof.

If the first material is an alloy of the first metal, such as an alloy of tungsten, osmium or iridium, the first metal constitutes the major constituent of the alloy. Thus, the first metal constitutes at least 50% by weight of the alloy, more preferably at least 60% and at least 70% by weight. In particularly preferred embodiments, the first metal constitutes at least 80%, preferably at least 85%, such as at least 90% or about 95% by weight of the alloy.

The second material does not have to have the high radiation attenuating capability of the first material but is mainly selected for being able to support the radiation attenuating inner leaf portion 12, 22. The second material should therefore have mechanical properties of being able to be mechanically connected to the first material inner portion 12, 22. Furthermore, in order to reduce the weight and cost of the collimator 1, the second material is preferably selected among inexpensive light metals and metal alloys. Thus, the second metal of the second material has an atomic number this is lower than the atomic number of the first material. The second material preferably has an atomic number of 30 or less according to the periodic table of the elements.

The second material preferably has a comparatively lower, more preferably much lower, density than the first material. For instance, the density is preferably no more than 12 g/cm$^3$, more preferably no more than 10 g/cm$^3$, such as about 8 g/cm$^3$ or below and therefore also includes low density metal and metal alloys with density of below 5 g/cm$^3$. Preferred materials of the remaining leaf portions 14, 24 include steel (density about 7.75-8.05 g/cm$^3$) and aluminium (Al, density about 2.70 g/cm$^3$).

The collimator leaves 10, 30, 40 preferably have a thickness (T, see FIG. 3) in the direction of an applied radiation beam in the range of about 10 mm to about 50 mm. Generally, thin leaves 10, 30, 40 with a thickness (T) of only about 15 to 25 mm in the direction of the radiation beam can be utilized. Correspondingly, the length (L, see FIG. 1) of a collimator leaf 10 can be from about a few centimeters up to about 30 centimeters, or even larger, and the corresponding width (W, see FIG. 3) of a leaf 10 could be about 1 to 20 mm. The length L and width W of the collimator leaf 10 is mainly determined based on the position of the collimator 1 relative the patient and the radiation target.

The high attenuating inner portions 12, 22 of the leaves 10, 20 only constitutes a minor portion of the total leaf volume. Thus, the inner portion 12, 22 does not constitute more than 40 volume percentage, preferably no more than 30 volume percentage, such as no more than 25, 20, 15 or 10 volume percentage of the collimator leaf 10, 20.

As is well known in the art of multi-leaf collimators, the leaves 10 of the collimator 1 are preferably individually adjustable, i.e. can be pushed towards each other or be retracted from its associated leaf 20 of the leaf pair 5. The leaf movement can be linear along the longitudinal axis of the leaves 10, 20. Alternatively, the leaves 10, 20 can be individually moved along non-linear paths, such as a curve path, which is all well-known in the art. FIG. 1 illustrates some collimator leaves pushed together to prevent any significant radiation from passing through the collimator part occupied by those leaves. However, some of the central leaves are retracted slightly from each other to form an opening in the collimator 1, through which a radiation beam can be passed and simultaneously be collimated. In this way, the first leaf portions 12, 14 will sharpen the penumbra at the edge of the applied radiation beam in order to minimize the dose at healthy tissue outside of an intended target volume, which is described further herein.

Figure 3:
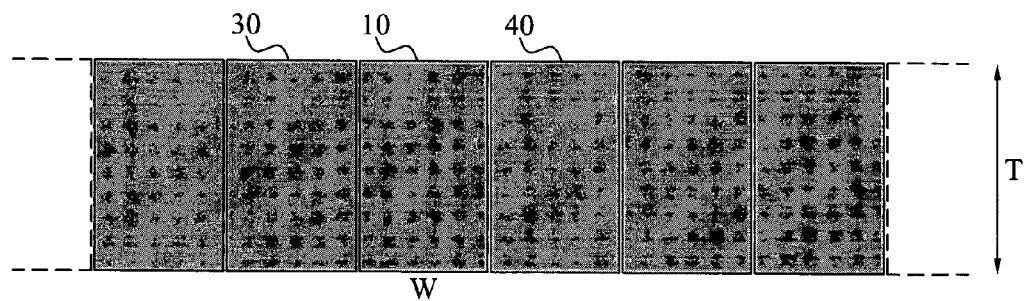
FIG. 3 is a frontal view of an embodiment of a multileaf collimator of the present invention along the line A-A in FIG. 1.

FIG. 3 is a frontal view of an embodiment of the multileaf collimator along the line A-A in FIG. 1. As can be seen in the figure, neighboring or adjacent collimator leaves 10, 30, 40 are provided close together, preferably touching each other's side surfaces. This tight fitting of the collimator leaves 10, 30, 40 reduces the amount of radiation that can unintentionally leak between adjacent leaves 10, 30, 40.

Figure 2:
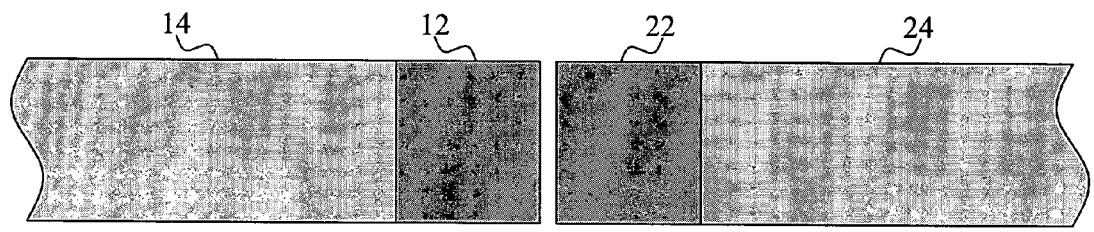
FIG. 2 is a schematic overview of a pair of leaves of a multileaf collimator according to an embodiment of the present invention.
Figure 4:
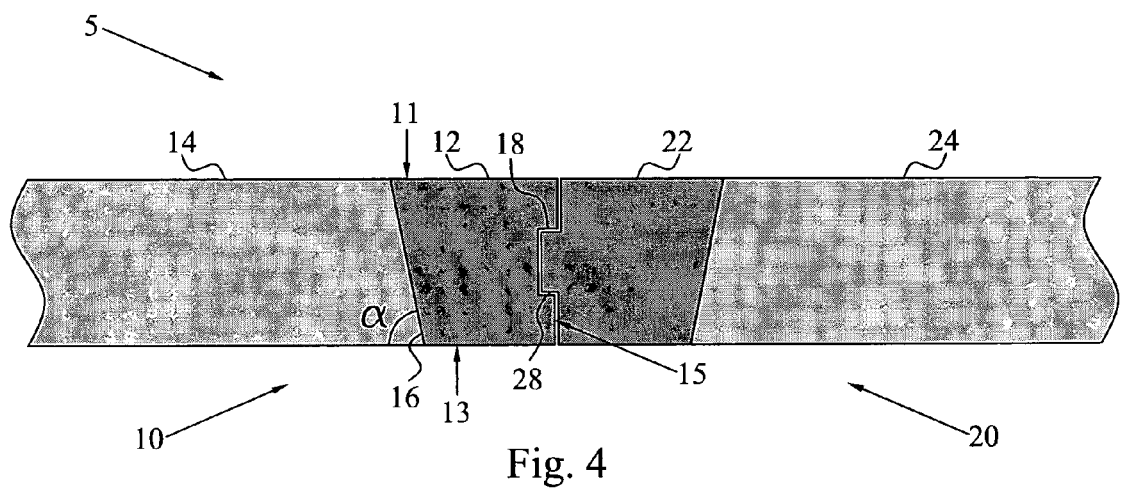
FIG. 4 is a schematic overview of a pair of leaves of a multileaf collimator according to another embodiment of the present invention.

According to the leaf pair 5 embodiment in FIG. 2, the inner high radiation attenuating leaf portions 12, 22 could have a cross-sectional configuration in the form of a quadrate or rectangular. FIG. 4 illustrates another possible solution for the inner radiation-attenuating leaf portion 12. An upper portion 11 of the inner leaf portion 12 extends a first distance from the leaf end 15 and into the collimator leaf 10. A corresponding opposite lower portion 13 of the inner leaf portion 12 extends a second, shorter distance into the collimator leaf 10. As a consequence, the side 16 of the inner leaf portion 12 facing the low-attenuating remaining leaf portion 14 is non-perpendicular to the longitudinal axis of the leaf 10, or expressed differently, an angle α between the side 16 and the longitudinal axis (or lower side of the leaf 10) is less than 90° but of course larger than 0°. Depending on the desired angle, the upper portion 11 can have a distance of at least 15 mm, while the lower portion 13 has a distance of at least 2 mm, such as at least 5 mm but is shorter than the upper portion distance. A typical example could be to have an upper high attenuating portion length of about 15 mm and a corresponding lower high attenuating portion length of about 10 mm. Such configuration of the inner portion 12 minimizes the safe size of the portion for penumbra trimming and radiation beam blocking point of view.

FIG. 4 also illustrates another preferred characteristic of the high-attenuating inner leaf portion 12, 22. An end side 15 of the inner portion 10 facing the other leaf 20 of the leaf pair 5 comprises a groove 18 designed for engagement with a matching shoulder 28 protruding from the high-attenuating inner leaf portion 22 of the other leaf 20. This design of opposite leaf ends reduces unintentional penetration of radiation through the leaf pair 5, when the two leaves 10, 20 are in a closed position, pushed tight together.

Figure 5:
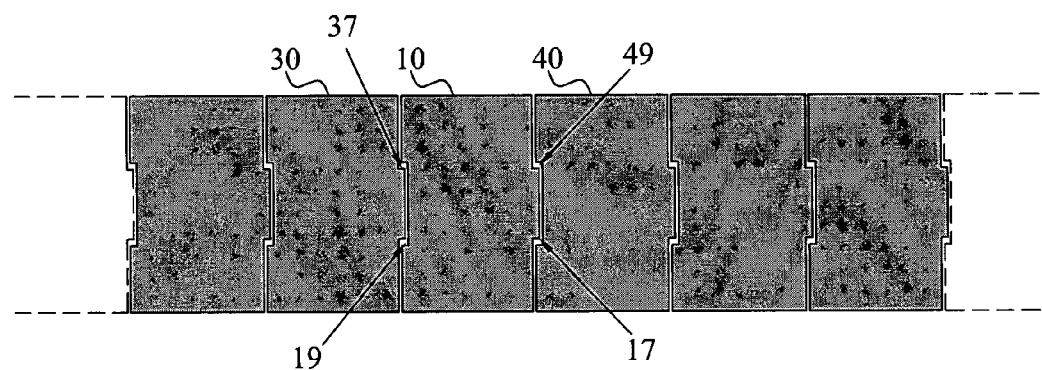
FIG. 5 is a frontal view of another embodiment of a multileaf collimator of the present invention along the line A-A in FIG. 1.

FIG. 5 is a frontal view of another embodiment of the multileaf collimator 1 along the line A-A in FIG. 1. In this embodiment, a first longitudinal side of the collimator leaf 10 facing a first neighboring leaf 40 comprises a longitudinal shoulder adapted for running in a matching longitudinal groove 40 of a facing longitudinal side of the first neighboring leaf 40. A second opposite longitudinal side facing a second neighboring leaf 30 is equipped with a longitudinal groove 19 adapted for engaging a matching longitudinal shoulder 37 provided at the facing longitudinal side of the second neighboring leaf 30. This collimator leaf design reduces the risk of unintentional leakage of radiation through the small (minute) space between neighboring leaves 10, 30, 40 in the collimator.

The concept of using shoulder and matching groove in FIGS. 4 and 5 can of course be extended so that one collimator leaf comprises multiple grooves, multiple shoulders or at least one groove and at least one shoulder.

The outcome of a radiobiologically optimized treatment plan can be considerably improved by modulating the intensity of the incoming beams. Such modulated beams can be achieved in several ways, from the utilization of simple compensator techniques to dynamic multileaf collimation and scanning beam systems. The most rapid and flexible technique for non-uniform dose delivery is provided by electromagnetic scanning of the elementary photon, electron or ion beams in combination with dynamic multileaf collimation. If the elementary beam is sufficiently narrow, i.e. with a FWHM (Full Width of Half Maximum) less than about 15 mm, the influence of the collimator on the therapeutic beam is quite low and may be viewed as negligible or, at least, be simplified considerably in connection with analysis of dose distributions.

The multileaf collimator of the invention is thus, in a preferred embodiment, designed for optimal use with narrow scanned beams. Simultaneous optimization of the scanning pattern and of the settings on the multileaf collimator automatically steers the elementary beam towards the opening of the collimator, thus providing the narrowest penumbra and most effective utilization of the beam. Consequently, the need to modulate the intensity of the beam by dynamic collimation is reduced in a narrow beam scanning system.

Instead, the task of the collimator becomes to protect the patient laterally and to sharpen and cut the tails of the elementary scanned beam. With this new role, the thickness of the collimator can be decreased to only a few centimeters of tungsten, as an illustrative but non-limiting example, and there is no need for focusing edges. Such a collimator is also suitable for trimming of light ion penumbra, since the range of carbon ions with an energy of 400 MeV/u is around 27 mm in tungsten, in contrast to 262 mm in soft tissue. With such penumbra trimming, the fragment tail beyond the Bragg peak will be quite small and almost negligible, see FIG. 13. This FIG. 13 illustrates the Bragg curve for a typical broad therapeutic carbon beam with energy of 400 MeV/u impinging on a tungsten collimator 30 mm in thickness. These calculations were performed employing the Shield-hit Monte Carlo code. A collimator of this thickness stops the primary carbon beam completely.

Furthermore, the distance between the source and the isocenter can be shortened in order to decrease the size of the elementary beam and thereby enhance the resolution of the intensity modulated beam. For instance, such reduction of the FWHM of the elementary photon beam to approximately 10 mm can be employed to increase the efficiency even further.

For all narrow scanned pencil beam applications involving photons, electrons or light ions, a collimator edge with a thickness of 15-30 mm in the direction of the beam should generally be sufficient. Approximately 15 mm is thick enough for high-energy leptons (positrons and electrons), whereas the hadrons (protons and light ions) will require leaf edges that are slightly thicker. In the case of very narrow high-energy scanned hadron beams, leaf collimation may not be particularly important.

However, when the penumbra of the pencil beam is enlarged in order to minimize the scan density, penumbra trimming is still valuable. Therefore, a collimator with a 15-25 mm leaf of osmium or tungsten may be appropriate for universal use. Furthermore, the low leaf height has the advantage of reducing edge scatter resulting from glancing incidence, which could be further minimized utilizing an edge with a slight divergence of about 5 degrees [2, 3].

Such a multileaf collimator is very light and fast compared to those of existing designs. In comparison to the multileaf collimators commonly used, the distance between the plane of this collimator and the source is reduced by approximately half, which decreases the surface area of the collimator by a factor of four. Relative to tungsten the thickness of the absorbing material in the collimator is only 20% and the density of steel only 40% as great and these values become even lower if aluminum is used. The total weight of the proposed collimator is thus only about 2% of that of the original leaf collimator, e.g., approximately 10 kg.

For such a small collimator, the leaf is thin and inter-leaf leakage thus higher than with a conventional multileaf collimator. However, through usage of shoulder-groove designs at the longitudinal sides of the leaves, such inter-leaf leakage is significantly reduced. Furthermore, with the simultaneous use of narrow scanned beams, only a very small fraction of the primary beam actually hits the collimator. Consequently, interleaf leakage is often negligible in practice.

FIG. 6 is a schematic overview of a radiation system and gantry 100 in which a multileaf collimator 1 according to the present invention can be arranged. The gantry 100 comprises a static gantry part 110 and a rotatable gantry part 120 that is rotatably supported by the static part 110. In this illustrative gantry example, the static gantry part comprises a klystron 112, such as a 50 MW klystron, for generating the driving force of a high-gradient linac 130 provided in rotatable gantry part 120. The klystron 112 is in communication with the linac 130 through a circulator 114. The linac 130 accelerates an electron beam 70 that is directed towards focusing and scanning magnets 140, 152, 154 forming a beam scanning arrangement 150 in the gantry 100. The energy content of the electron beam 70 exiting the accelerator 130 is preferably at least 20 MeV and more preferably at least 50 MeV.

The beam 70 is then directed towards a thin target 160 for the purpose of generating a photon-based radiation beam 60. More recently, the thin-target (target thinness of about 2 mm to about 5 mm) irradiation technique, which has the potential of scanning intense quasi-Gaussian photon beams of sizes down to 12 mm FWHM at 50 MeV has been developed [4]. This is achieved using a thin transmission target of low atomic number (preferably an atomic number no larger than 40, such as beryllium) and, thus, low electron scattering power so that broadening of the bremsstrahlung beam is minimized [5, 6]. Since its FWHM is inversely proportional to the incident electron energy, elevation of this energy from 50 to 60 MeV reduces the beam width even further.

In order to deflect the high-energy electron beam 70 transmitted through the thin target 160, a strong purging magnet 156 should be placed immediately below the target 160. In addition, the magnetic field needs to be changed rapidly if the electrons are deflected onto the same collector regardless of the direction of the photon beam 60. This collector should absorb the electron beam, the associated bremsstrahlung and higher-order secondary radiations such as scattered photons and neutrons almost completely. The geometrical size of the yoke and coils, as well as functionality and safety issues have been discussed previously [2]. The FWHM of the elementary photon beam at an SSD of 750 mm will be approximately 10 mm, which means that certain conventional beam-shaping devices, such as blocks, thick multileaf collimators and wedges, may be redundant. However, for safety reasons and in order to sharpen the penumbra, use of a thin multileaf collimator 1 of the invention may be desirable. Thus, the treatment head can be made very small and compact to maintain sufficient clearance between this head and the patient and to provide space for PET/CT source 175 and associated equipment. An optional but preferred high resolution dose monitor 170 may also be provided in the radiation head.

The radiation pencil beam 60 generated at the target and having passed through the multileaf collimator 1 of the present invention for penumbra shaping hits a target volume in a patient 80 positioned on a patient couch 190 arranged in connection with the radiation gantry 100. The collective operation of the beam scanning system 150 and the fast, light multileaf collimator of the present invention 1 allows the radiation beam 60 to be efficiently and safely scanned over a predefined area of the patient 80 for obtaining a rapid intensity modulated radiation therapy.

In a preferred embodiment, the gantry 100 can also be equipped with a detector 180, e.g. an electronic portal imaging device, for further verification of the accurate dose delivery. This detector 180 can operate together with or instead of the dose monitor 170. The detector 180 could instead be a detector for radiotherapeutic CT scanning using the CT scanner 175. Alternatively, the retractable detector unit could include both a CT detector and a portal imaging detector.

The gantry 100 illustrated in FIG. 6 should merely be seen as an illustrative gantry design, in which the multileaf collimator 1 of the invention can be arranged. As a consequence, the multileaf collimator 1 can be arranged in other gantry designs and radiation systems.

Furthermore, the electron generating source could instead be implemented in the stationary gantry part. Other accelerator embodiments, besides high-gradient linacs can be used, such as racetrack microtrons [8, 9].

The proposed unit for photon and electron therapy, see FIG. 6, is designed for rapidly adaptive, intensity modulated delivery of radiation with a well controlled three-dimensional distribution and is based on the unique narrow pencil beam scanning technology together with a new principle for verification of treatment involving advance imaging of the distributions of dose delivered by PET-CT distributions in combination with cone-beam radiotherapeutic computed tomography (RCT), electronic portal imaging and in vivo monitoring of dose delivery by PET-CT and planning on the basis of PET-RCT. However, the collimator of the invention is not limited to this particular therapy type nor to the particular system described above and illustrated in FIG. 6.

FIGS. 7A to 7F illustrate the operation of the radiation gantry in FIG. 6 by directing the narrow radiation beam from different incident angles to thereby provide a scanning of the penumbra-shaped beam over the target volume. By being able to rotate or turn the radiation head as illustrated in these figures, the collimator of the invention can actually be a single leaf pair collimator only comprising a single leaf pair.

Electromagnetic scanning with narrow bremsstrahlung beams requires a high-energy electron beam of low emittance for purposes of transport and photon focusing. In a recently proposed design, a racetrack microtron was mounted on the gantry in order to reduce the length of beam transport, as well as making the electron beam that hits the target always is rotationally invariant and is rapid to install [9]. Furthermore, use of a compact gantry would save space.

Several recent breakthroughs in research on high-gradient linear accelerators allow 50-100 MV/m accelerator gradients in both the S- and X-band regions. This development, stimulated in part by the suggestions for novel generation of electron and positron colliders in connection with high-energy physics at SLAC (Stanford), KEK (Japan) and CLIC (CERN, Geneva), was designed for large-scale industrial manufacturing, lowering the price considerably and making the mounting of a gantry on such accelerators of interest. Short structures require an extremely high power peak pulse and sophisticated engineering in order to transport the microwave from an external klystron to the accelerator mounted on the rotating gantry. It may also be possible to utilize a high-power magnetron mounted in the gantry, but in this case the electron beam probably needs to be accelerated twice in the same structure, as was done in the Reflexotron [10].

This treatment unit described above and disclosed in FIG. 6 can deliver optimized non-uniform beams in a very short time due to an efficient scanning system working together with the novel transmission target technique [5, 8]. In this fashion an elementary electron or photon beam can be positioned electromagnetically anywhere within a field of, for example, 40×40 cm$^2$ at the isocenter of the machine. Furthermore, the small collimator of the present invention allows for a shorting of the distance from the source to the isocenter, which will reduce the beam width even more, to approximately 10 mm.

FIG. 8 illustrates dose distributions of elementary 50 MV bremsstrahlung beams for different target designs. The narrowest photon beam will be generated using 70 MeV initial electron beam for instance from a short high power x-band linac mounted in the gantry.

Monte Carlo Calculations Using GEANT4

The object oriented Monte Carlo simulation toolkit GEANT4 [11, 12] was employed here to simulate particle transport through the thin collimator of the present invention. Various 50 MV photon beams and a 50 MeV elementary electron beam were utilized to simulate photon transmission and electron scatter effects, respectively, in association with collimator edges composed of various materials.

First, collimation of photon beams by collimators composed of aluminum and steel and with edges of tungsten or osmium was investigated. A stationary elementary bremsstrahlung beam was directed forward and the collimator edge positioned exactly at the central axis. Secondly, a collimator composed entirely of tungsten was utilized together with various incoming scanned beams. The incoming elementary photon beam was either stationary, scanned in parallel with or perpendicular to the collimator edges or moved both parallel and perpendicular to the collimator edge to generate a full and uniform beam. Moreover, the scan pattern was optimized to produce a uniform rectangular field of 5×10 cm$^2$ only at the opening of the collimator. Here, the scan pattern of the elementary photon beam was optimized employing an iterative deconvolution algorithm that minimizes overdosage while always avoiding underdosage [13]. This optimized scan pattern was then used by the GEANT4 toolkit to simulate transmission of a scanned photon beam through the collimator. The elementary photon beam was generated by a 50 MeV electron beam impinging on a 3-mm beryllium bremsstrahlung target, with programmed suppression of the transmitted primary electron beam of high energy (49.3 MeV). The forward stationary elementary beam was generated by at least 200 million electrons hitting the target, whereas the scanned beam was generated by 1 billion incident electrons.

A forward directed elementary 50 MeV electron beam was employed to simulate the in-scatter effect of electrons associated with edges made from different materials on a steel collimator.

FIG. 9 illustrates the Monte-Carlo (GEANT4) calculations of the transmission of forward directed bremsstrahlung through a collimator composed of different combinations of Al and Fe and with an edge of W or Os. The calculations for Al—W and Fe—W collimators are presented as dotted lines, those for Al—Os and Fe—Os as the solid (lower) lines and the uncollimated beam is shown as the solid upper line. The beam is scored at the isocenter and the collimator geometry depicted here is projected to this isocenter. As expected, the Fe collimator with a 700 osmium edge attenuates the incoming beam to a greater extent than does the Al collimator with a tungsten edge, due to the higher densities of Os and Fe. The tail of the narrowest beam is sharpened by both the tungsten and the osmium edge. The Al collimator with an Os edge adequately collimates a narrow scanned beam, whereas the Al collimator part serves almost only as a support for the edge. Thus, utilization of a low density material, such as aluminum, as the primary component of the collimator in combination with a tungsten or osmium tip is sufficient to produce an effective beam, where a somewhat higher increase in the fluency of the transmitted "penumbra" can be observed at the border between the tip and the main collimator.

Multileaf Collimation of Narrow Scanned Photon Beams

The influence of designs involving multileaf collimators and leaf tips composed of various materials on the characteristics of the scanned photon beam was also investigated. In this context, beam sharpening and the transmission of an elementary narrow forward directed pencil beam (3 mm Be) were examined with aluminium (Al) or steel (Fe) as the primary collimator material and tungsten or osmium in the collimator tip (see FIG. 9). Particle transport was determined by Monte Carlo simulation (GEANT4) and the beam was generated with a 50 MeV electron beam incident onto a 3 mm Be bremsstrahlung target. The forward directed elementary beam was first positioned exactly at the edge of the collimator.

With identical edge thickness, a relatively high density osmium edge attenuates the narrow beam to a greater extent than tungsten (Table III, FIG. 9). Moreover, utilization of a low density material such as aluminum as the primary component of the collimator in combination with a tungsten or osmium tip is sufficient to produce an effective beam, as shown in FIG. 9, where a somewhat higher increase in the fluency of the transmitted "penumbra" can be observed at the border between the tip and the main collimator.

FIG. 10 discloses profiles of scanned and stationary photon beams combined with a thin collimator edge. A stationary elementary beam (solid outer line) and a profile through a scanned beam in the y-direction without collimation (dashed outer line) are shown. The scanned beam becomes slightly larger due to its imperfect Gaussian characteristics. The inner lines illustrate a collimated stationary beam (inner solid line) and a profile through a beam scanned along the collimator edge in the y-direction (inner dashed line). The energy fluence transmission through the thin collimator never exceeds 20% of the primary incident beam, which is already narrow, and can therefore be employed whenever needed to sharpen the incident field.

FIG. 11 illustrates characteristics of collimated and scanned elementary photon beams in combination with the collimator with a thin edge. Monte Carlo GEANT4 calculations were used to simulate transport through the collimator edge. The solid lines depict beams scanned in x-direction only, while dashed lines show beams scanned in the both x- and y-directions. The projection of the collimator edge is positioned at the isocenter (x=0 mm). The inner solid line illustrates an optimal scan for a desired 0-50 mm uniform field with minimal overdosage in combination with the collimator, the middle solid line the same situation without the collimator, and, finally, the outer solid line shows the consequence of unnecessary 50 mm overscan in the −x direction, which results in the expected 20% uniform transmission of the primary beam. Clearly, the 80-20% penumbra for the collimator together with the scanned beam is sufficiently small for clinical use, in some cases even without using the thin collimator.

The build up of tails in the integral fields for different scan patterns is illustrated in FIGS. 10 and 11. First, a stationary elementary beam was directed at the edge of the tungsten collimator (solid line, FIG. 10) and scanned along the collimator tips (dashed line). This dashed line demonstrates that the resulting integrated beam is somewhat larger than the stationary beam (solid line), due to its non Gaussian tail (the projected distribution of a Gaussian beam coincides with the elementary beam). The 80-20% fluence penumbra is no more than four our millimeters.

When the elementary beam is scanned perpendicular to the collimator edge, the transmitted intensity penumbra is, as expected, approximately 20% (Table III and solid line FIG. 11). When the scan pattern generates a full uniform beam (short dashed line), (i.e. with scanning both in parallel and perpendicular to the edge of the collimator), the transmitted fluence of around 20% is somewhat higher than that obtained by scanning only perpendicular to the collimator edge. The optimally scanned beam is located solely within the beam opening in order to minimize treatment time and leakage from the collimator onto the patient. The resulting fluence below the collimator edge will be maximally 20% somewhere a few millimeters away from this edge and rapidly drop to zero at greater distances.

Optimization of the Outcome of Photon Beam Treatment

In this case, only one optimal multileaf setting was employed together with the different collimator designs, beam qualities and delivery techniques, i.e., uniform beams, scanned beams involving a full range target composed of BeW (FWHM=75 mm), a transmission target technique using 3 mm Be (FWHM=30 mm), and, finally, reduction of the beam size with a thinner target, higher energy and shorter distance to obtain an FWHM of 15 mm. As the ultimate high resolution benchmark, the size of the beam was reduced to zero in order to obtain a point monodirectional pencil beam.

First, the treatment outcome with collimator designs involving tungsten 15-70 mm in thickness was optimized. The thickest collimator, which is double focusing, is used today in the MM50-system [14, 15] at Karolinska University Hospital, Sweden and was employed here as an almost perfect collimating system, but with variable width of the leaves, to obtain an upper benchmark [16]. The average photon transmission of a 50 MV BeW photon beam by such a collimator leaf is far less than 1% and has been neglected here since it will only influence a thin rim outside of the beam opening. The second collimator consisted of 20 mm tungsten in the direction of the beam resulting in approximately 90% absorption and 10% transmission of the incident photon beam. The third collimator was composed only of 15 mm tungsten, allowing transmission of 20% of the incident beam. In addition, this latter collimator was modified to obtain a lighter and simpler device for scanned beams by replacing all of the tungsten by steel except at the edges facing the beam (FIGS. 14 and 9).

As much as 60% of the full beam is transmitted through 15 mm of steel. Obviously, conventional filtering of a uniform beam cannot be used with either of these thin collimators, since the whole body of the patient would be showered with transmitted photons, as seen in the upper panels of FIG. 14. With the present MM50 collimator design [14, 15] with a collimator of thickness 70 mm, the outcome of treatment for uniform beams becomes about 72% while this value was reduced to 65% in the case of the collimator composed of 15 mm thick tungsten. Interestingly, the treatment outcome is only reduced to 71% when the transmission through the collimator is on the order of 10% (with 22 mm thick tungsten). The explanation for this is simply that proximity to 10% isodose line is associated with a large degree of tolerance by the normal tissue. Treatment of the same patient with uniform beams using the collimator composed of 15 mm steel and with 15 mm tungsten edges obviously leads to a poor result, due to the far too high dose experienced almost everywhere in the patient (upper panel in FIG. 14), as a consequence of which the treatment outcome was reduced to approximately 30%, i.e., by more than half in comparison to the MM50 collimator.

When optimized scanned beams are used, the treatment outcome rapidly improves as the elementary beam is made narrower. This is particularly true in the case of the steel collimator, since the elementary beam will be directed towards the collimator opening by the algorithm for optimization of the scanning pattern. Optimal scanning employing relatively broad elementary bremsstrahlung beams, such as those generated from a BeW target, enhances the treatment outcome by 6% for the thinnest collimator made of tungsten alone and by more than 30% for the collimator composed of steel with tungsten edges. The improvement in treatment outcome upon replacing a uniform with a scanned beam is not as dramatic with collimators constructed from thicker material, clearly demonstrating that most lateral protection of organs at risk is provided by the scanned beam, rather than by the collimator. The combination of scanned beams using a full range target combined with a collimator made of aluminium does not result in an acceptable treatment outcome.

When the width of the narrow scanned beam is reduced to below 15 mm, the treatment outcome with the thinnest collimator made of 15 mm uniform tungsten reaches a level of 81%. This value is slightly lower for the steel/tungsten collimator and 82% for the thickest tungsten collimator. With the narrowest beam the improvement in treatment outcome flattens out, exhibiting almost the same value as when the collimator possesses full thickness for the beam. In the case of the narrowest pencil beams, the difference between a collimator made of steel with tungsten edges and a collimator composed completely of tungsten is negligible, since the scanned beam itself modulates the incoming beam both longitudinally and laterally. Thus, the collimator of the present invention can be used instead of a heavy, expensive and cumbersome tungsten collimator for such pencil beam radiation systems.

Interestingly, a relatively good treatment outcome is attained with the narrowest scanned beam (FWHM=16 mm) in the absence of a collimator (first column in FIG. 14). In general, the findings concerning optimization using materials of higher density, such as osmium, to construct the edge are similar, although an edge of osmium can be somewhat thinner than when using tungsten. A collimator edge of high density is desirable for safety reasons, i.e., for absorbing the bremsstrahlung, electron and ion pencil beam tail, as well as for minimizing the out-scatter of this edge.

FIG. 14 illustrates optimization of the outcome of treatment with primary beams of varying quality utilizing uniform and scanned beam delivery and simultaneous optimization with a single multileaf setting for collimators of different thicknesses and edges as well as without collimation. The leakage is expressed as the percentage of the primary incident energy fluence that is transmitted. Three different elementary beams with FWHM values of 80, 32 and 16 mm were used for scanning (middle panels) in comparison to uniform beams (upper panel, infinite FWHM) and monodirectional point pencil beams (lower panel, FWHM=0 mm). The first column illustrates the optimization with scanned beams only, the second column optimization with a scanned beam together with a steel collimator with tungsten edges and the other three columns optimization with collimators made of only tungsten of different thicknesses.

Multileaf Collimation of Scanned Electron Beams

The thin flat leaf collimator of the present invention is also ideally suited for sharpening the penumbra of narrow elementary scanned electron, as well as photon beams. Poor design of the collimator and, in particular, of its edge may severely influence the dose distribution in the patient as a consequence of electron scattering by the collimator edge as well as bremsstrahlung generated in the collimator [17, 18]. A focused collimator edge decreases the in-scatter of nonparallel electrons, but such in-scatter from an unfocused edge can also be largely eliminated by hiding the edge from the source of the beam.

The build-up region is influenced by electrons that hit the collimator on the side of the source and are then scattered out laterally from the edge to contaminate the beam. The mean energy of such electrons is approximately 40% of that of the incident electrons and is independent of edge material. The dose absorbed as a result of electron scattering is inversely proportional to the density of this edge and almost independent of the electron energy and atomic number [17]. Thus, the edge of the collimator should be made of dense material such as tungsten or even osmium (Table III, FIG. 12).

FIG. 12 illustrates the significance of employing a high density edge to minimize the collimator electron in-scatter in connection with electron therapy. All beam transport was simulated with the GEANT4 transport code. The solid line depicts an uncollimated elementary electron beam for beam scanning (at SID 70 cm) from a compact treatment head. In this case, the beam was transported in vacuum in order to observe the effect of the collimator edge more clearly. The collimator was composed of steel (Fe) with a 15 mm, high density edge of tungsten (dotted line) or osmium (dashed dotted line). The steel edge was used as reference (dashed line). The in-scatter by steel is roughly 5-fold higher than by tungsten or osmium. For the osmium edge electron in-scatter is somewhat lower than with tungsten.

For scanned electron beams, contamination by bremsstrahlung produced in the collimator material is of lesser significance, since more than 95% of the total primary beam is directed at the collimator opening and only the tail of the incident elementary beam need be collimated away. Ideally, to minimize such bremsstrahlung, the region where the electrons enter should be constructed of a material with a lower atomic number which however, would unfortunately increase the lateral in-scattering of electrons. At the same time, such in-scattering could be largely eliminated by the use of an edge lining of high density and thickness $z_1$ (see Table III) [17].

Multileaf Collimation of Light Ion Beams

In the case of light ions, the design and operation of the collimator are largely dependent on the manner by which the incident beam is generated and the technique for range modulation employed. The most pure dose delivery technique is by using the narrow light ion spotscanning technique and range modulation by the variable extracted almost monoenergetic energy elementary beam from the accelerator. Here, the collimator of the invention functions in a manner similar to the scanning technique for narrow elementary electron beams. With narrow ion beams, the collimator acts more as a safety device, both attenuating head leakage and sharpening the tail of the lateral beam in connection with treatment. A collimator leaf edge consisting of 30 mm thick tungsten or, even better, of osmium (in order to minimize edge scatter [17]), completely absorbs most light ion beams of a range of about 26 cm in water (Table III).

The lateral scatter in connection with light ion beams can be calculated quite accurately on the basis of a few well founded assumptions. Assuming that the distribution of multiple scattering [19] is Gaussian, the radius outside of which less than 1% of the incoming particles are present, $R_1$, is defined by the equation 5:

$$\int_{R_1}^{\infty} \frac{e^{-r^2/\bar{r}_z^2}}{\pi \bar{r}_z^2} \leq 0.01 \quad (5)$$

where r is the radial displacement from the central axis of the beam (z-axis) and $\bar{r}_z^2$ is the mean square radius of the radial distribution at depth z. Equation (5) can be integrated analytically [17, 19] to yield the expression 6:

$$R_1 \geq \sqrt{\bar{r}_z^w \ln(100)} \quad (6)$$

Since for light ion beams exhibits its highest value at the projected range in the vicinity of the Bragg peak, equation 3 can be simplified one step further:

$$R_1 \geq \sqrt{\ln(100)} \sigma_r \quad (7)$$

where $\sigma_r$ is the variance of the radial distribution of the pencil beam calculated at the Bragg peak [19]. This value is distinct from the corresponding value for electrons, which exhibit their maximal fluence and dose at approximately half the range ($z_1$) [17]. The radius $R_1$ for different collimator materials (denoted m), as well as for different projectiles can then be approximated by simple linear scaling with water (denoted w) on the basis of the mass scattering power [19, 20] as follows:

$$R_{1,m} = R_{1,w} \sqrt{\left(\frac{T}{\rho}\right)_m / \left(\frac{T}{\rho}\right)_w} \approx R_{1,w} \left(\frac{\rho_w}{\rho_m}\right) \frac{Z_{A,m}}{Z_{A,w}} \sqrt{\frac{M_{A,w}}{M_{A,m}}} \quad (8)$$

(assuming that no screening of the nucleus by the orbital electrons occurs and that the size of the nucleus is negligible).

The $R_1$ values calculated for different collimator material and projectiles are documented in Table III. It can be seen that the most pronounced lateral scatter is obtained with the lightest ion beams of lowest atomic number for which the radial variance is highest. Furthermore, the higher the mean density of the collimating material, the smaller the area along the front surface of the collimator that can scatter ions away from the front edge, again pointing to osmium as the most interesting collimating material.

Quite often, in order to avoid having to deliver a very large number of beam spots in the total scanning pattern, light ion pencil beams are not generally focused so as to obtain minimal diameter. With such focusing multileaf trimming of the penumbra allows significant improvement of the quality of the beam at its edge, as well as enhanced elimination of over-scanning. Similarly, when ion beams accelerated in a cyclotron are decelerated for appropriate range modulation, the emmitance selection system will be more efficient when slightly larger beam spots are allowed.

As is illustrated in Table III, the preferred materials of the penumbra-trimming portion of the leaves have low values ($Z_1$ in the table) of any longitudinal spread of an incident radiation beam in the trimming material. This means the risk of contaminating the radiation therapy beam through such spread radiation originating from multiple scattering in the materials is therefore significantly reduced.

TABLE III radiation-related material characteristics

| COLLIMATOR | | | PHOTONS | | | | | | | ELECTRONS | | | | LIGHT IONS | | | | |
|---|---|---|---|---|---|---|---|---|---|---|---|---|---|---|---|---|---|---|
| | | | 50 | | | 70 | | | | | | | | $^1$H | $^9$C | $^{11}$C | $^{12}$C | $^1$H | $^{12}$C |
| Energy | | | MV | | | MV | | | | 50 | | 70 | | 210 | | 400 | | | |
| Quantity | | | $\mu/\rho$ | | | $\mu/\rho$ | | | | MeVe$^-$ | | MeVe$^-$ | | MeV | | MeV/u | | 210 | 400 |
| Unit | Z | $\rho$ g/cm$^3$ | $10^{-2}$ cm$^2$/g | $t_{1\%}$ | $t_{10\%}$ mm | $t_{20\%}$ | $10^{-2}$ cm$^2$/g | $t_{1\%}$ | $t_{10\%}$ mm | $t_{20\%}$ | $z_{csda}$ mm | $z_1$ | $z_{csda}$ mm | $z_1$ | R mm | | | $R_1$ mm | |
| H$_2$O | 7 | 1.0 | 1.88 | 2450 | 1220 | 856 | 1.85 | 2489 | 1240 | 870 | 198 | 144 | 255 | 176 | 278.5 | 209.0 | 255.4 | 278.7 | 15.1 | 4.2 |
| Be | 4 | 1.8 | 1.22 | 2040 | 1020 | 713 | 0.93 | 2677 | 1338 | 935 | 143 | 113 | 187 | 141 | 186.7 | 140.5 | 171.8 | 187.4 | 7.0 | 1.9 |
| C | 12 | 1.7 | 1.64 | 1652 | 826 | 577 | 1.53 | 1370 | 684 | 478 | 134 | 98 | 172 | 93 | 139.5 | 104.9 | 128.2 | 139.8 | 19.8 | 5.5 |
| Al | 13 | 2.7 | 2.18 | 782 | 391 | 273 | 2.18 | 782 | 391 | 273 | 77.4 | 48 | 96.2 | 56 | 133.2 | 99.4 | 121.5 | 132.6 | 9.0 | 2.5 |
| Steel | 26 | 7.8 | 3.15 | 187 | 94 | 66 | 3.33 | 177 | 89 | 62 | 23.8 | 12 | 28.5 | 13.6 | 50.4 | 37.5 | 45.8 | 50.0 | 4.3 | 1.2 |
| W | 74 | 19.3 | 5.64 | 42 | 21 | 15 | 6.18 | 39 | 19 | 13 | 7.8 | 2.8 | 8.9 | 3.1 | 28.1 | 20.8 | 25.4 | 27.7 | 2.7 | 0.7 |
| Os | 76 | 22.6 | 5.70 | 36 | 18 | 12 | 6.36 | 32 | 16 | 11 | 6.7 | 2.4 | 7.6 | 2.6 | 24.5 | 18.1 | 22.1 | 24.1 | 2.4 | 0.6 |
| Hg | 80 | 13.5 | 5.88 | 58 | 29 | 20 | 6.48 | 52 | 26 | 18 | 10.9 | 3.9 | 12.4 | 4.3 | 41.2 | 30.4 | 37.1 | 40.5 | 4.1 | 1.1 |
| Pb | 82 | 11.4 | 5.93 | 68 | 34 | 24 | 6.61 | 61 | 31 | 21 | 12.8 | 4.6 | 14.6 | 5.0 | 49.4 | 36.5 | 44.6 | 48.6 | 4.9 | 1.3 |
| U | 92 | 18.9 | 6.22 | 39 | 20 | 14 | 6.95 | 35 | 18 | 12 | 7.6 | 2.6 | 8.7 | 2.9 | 30.6 | 22.6 | 27.6 | 30.1 | 3.1 | 0.8 |

Radiobiological Optimized Treatment Planning

The influence of different collimator designs on the outcome of treatment with scanned beams was examined here with our treatment planning pencil beam optimization algorithm [21]. This versatile algorithm employs constrained iterative optimization of the settings on the multileaf collimator and the scanning pattern simultaneously [21-25]. For each collimator design, a relatively simple transmission function that takes into account only the attenuation of the primary beam is incorporated into the algorithm. For the sake of simplicity, this transmission function involved only a tungsten edge with a width of 15 mm and no tapering such as that in the more optimized design depicted in FIG. 1B.

Our optimization algorithm [13, 21] utilized the probability of complication free control of the tumor, P+, as an indicator of the treatment outcome. The target volume was a stage IV cervix cancer with spreading to lymph nodes and a volume of 64×64×24 cm$^3$ with a cubic voxel size of 0.5×0.5×0.5 cm$^3$ was studied. Relevant radiobiological data were obtained from the literature [16, 26, 27].

In order to demonstrate the efficiency of this collimator design in combination with pencil beam scanning, optimal radiobiological treatments of an advanced cervix cancer was simulated. Different geometrical collimator designs were tested for bremsstrahlung, electron and light ion beams. With a 10 mm half width elementary scanned photon beam and a steel collimator with tungsten edges, it was possible to make as effective treatments as obtained with intensity modulated beams of full resolution, i.e. near 5 mm resolution in the fluence map. In combination with narrow pencil beam scanning, such a collimator may provide ideal delivery of photons, electrons or light ions for radiation therapy synchronized to breathing and other organ motions. These high-energy photon and light ion beams may allow 3-dimensional in vivo verification of delivery and thereby clinical implementation of the BIOART approach using Biologically Optimized 3-dimensional in vivo predictive Assay based adaptive Radiation Therapy [33].

Fast Intensity Modulated Treatment

The continuously increasing incidence of cancer and associated costs for health care call for more rational and cost-effective methods of treatment. Busy and efficient clinics require more rapid, more accurate and most cost efficient techniques for dose delivery. Conventional radiation treatments employing static uniform beams that are still in use at most centers for radiation therapy centers take approximately 10-15 minutes from the time the patient enters the treatment room until he/she has left. Most of this time is devoted to positioning the patient, quality assurance and care. The period of radiation, including rotation of the gantry, is about 1-3 minutes, depending on the type of equipment and technique employed. Most treatment units of this type are designed to treat as many patients as possible with a given time-frame.

Introduction of intensity modulated radiation treatment into the clinic requires more sophisticated quality assurance with respect to the delivery of beams, due to uncertainties in the positioning of the patient and organ movement. Most equipment in use today involves relatively old gantry technology and beam shaping designs, even though beam modulation has been improved considerably by dynamic multileaf collimation. Consequently, more time must be spent both on positioning the patient and delivering the IMRT treatment.

More integrated solutions, in which planning of the treatment, movement of the target (e.g. due to respiration) and the characteristics of the beam are integrated on-line, would be highly advantageous. Today, these parameters are integrated primarily by using external markers and margins for positioning. The relationship to the actual clinical target volume during treatment is less well-defined and generally based on addition of an internal margin and, in some cases, stereotactic beam alignment on small targets [28].

Today, most new therapy units being installed are capable of performing IMRT, being equipped with multileaf collimators that can be operated in a dynamic mode with segmental steps and the shoot technique and, in certain cases, even continuous dynamic velocity modulation. Such velocity modulation of the intensity of multileaf collimation is most rapid and exhibits high resolution. However, the period of irradiation required is still proportional to the sum of the differences between consecutive peaks and valleys in profile of the beam delivered. Thus, a highly complex irradiation involving multiple peaks in the beam profile, the time of irradiation may be several-fold longer than that require for conventional treatment with a uniform beam. In contrast, a scanned ultra narrow beam, on the other hand, with an average rate of dosage similar to that employed for a broad scanned or conventional flattened beam will be only minimally influenced by the complexity of the incident energy fluence profile. Fast pencil beam scanning systems are approximately three orders of magnitude faster than mechanical devices such as those involving blocks or multi-leaf collimation and can produce a beam with high resolution within a second. The novel collimator of the present invention having a low weight described herein is also potentially much faster than conventional multileaf collimators, with potential speeds of approximately 10 cm/s or more, and furthermore needs to move shorter distance to obtain only a few multileaf settings.

4D-intensity modulated radiation therapy involving adaptive therapy approaches or other more dynamic techniques that take breathing and/or the movement of internal organs into account requires more rapid techniques for delivery in order to be cost-effective. In the case of intensity modulated beams employing dynamic multileaf collimation, the required irradiation time is proportional to the complexity of the modulation; whereas, in contrast with narrow scanned beams, this irradiation time is almost independent of the dose variations in the beam and more dependent on the total mean energy imparted. With increased use of strong intensity modulation, the irradiation time with conventional IMRT techniques will account for a larger portion of the total treatment time.

It has been shown [9] that for therapy involving fast modulation of the intensity of photon beams, electromagnetic scanning is advantageous. Here, characteristics of the novel multileaf collimator designed to narrow scanned elementary photon pencil beams have been presented in connection with an advanced cervix cancer. For most narrow elementary beams, where the influence exerted by the collimator is relatively low, a steel or aluminum collimator with tungsten or osmium edges is sufficient to attain the best possible outcome of the treatment. Our findings strongly motivate the development of such fast collimators. Together with narrow scanned beams, such collimators are potentially useful for real time adaptive therapy and interestingly very similar designs may be employed for therapy with photons, electrons and light ions.

Other Gantry Designs

As was mentioned in the foregoing, the collimator of the present invention can be used in connection with the Orbiter system [29]. The key characteristics of the Orbiter are:
high speed delivery of high precision conformal, intensity modulated radiation therapy;
accurate patient positioning through built in laser camera [30];
automated fixed field "multi segmented" therapy;
dynamic intensity modulation with high resolution Multi-Leaf Collimator ("MLC") or a newly developed areal modulator;
no risk of collision between treatment head and patient;
beam clearness in all gantry angels; and
high reliability and low cost per treatment.

Orbiter has currently only one energy—the 6 MV photon beam. The accelerator is placed in line close to the target in the treatment head. The gantry is capable of unprecedented high-speed rotation. The system will be designed for gantry speeds of up to 10 rotations per minute, which means 10 times faster than existing systems. The design of the gantry will allow fast acceleration and retardation.

The gantry has two support points. This implies better mechanical gantry stability, which means better isocentric precision. The gantry has no end-up, allowing full rotational freedom. This means that the shortest possible route from one gantry angle to the next can always be chosen. This will save time. In addition, it may facilitate rotational treatment techniques such as arc therapy or tomotherapy, although the Orbiter is not primarily designed with such treatment techniques in mind.

The MLC is designed for intensity modulation. The field size should be at least 30 cm×40 cm, with a projected leaf width of 7.5 mm. The leaves should have a very large over travel, 150 to 200 mm, so that large field sizes can be intensity modulated. The leaf speed should be high, more than 25 mm per second, to facilitate effective delivery of intensity modulated treatment fields. Optionally the system can be equipped with a two dimensional hexagonal areal intensity modulator allowing fast beam flattening and/or intensity modulation.

Collision between gantry and patient is not possible, because all moving parts are hidden inside the gantry. The couch will only be adjusted small distances in the lateral and vertical direction.

The couch has a very low radiation cross-section in the treatment area, allowing beams to be delivered from all gantry angles without restriction. This is made possible by the fact that the couch has two support points.

The non-existent beam transport results in low cost and high reliability.

The electronic portal imaging device based on GEM technology is an integral part of the system and enclosed inside the system. It will produce both diagnostic and therapeutic images of high quality The Orbiter can be interfaced to the most commonly used Treatment Planning Systems. The Orbiter can also be interfaced to the most common verification systems. The collimator of the present can advantageously be used in the Orbiter system, preferably also together with the dynamic beam intensity modulator disclosed in the document [31].

In a further implementation embodiment, the collimator of the invention is used in connection with the BioARTist system described herein.

More than half of all cancer patients benefit from radiation therapy and the number is steadily increasing. Modern biologically based intensity modulated treatment techniques might improve the treatment outcome by as much as 20-30% for advanced resistant tumors. More advanced diagnostic and therapeutic instruments are necessary particularly for complex hypoxic or otherwise radiation resistant tumors to improve the uncomplicated tumor control. Sensitive and specific tumor imaging techniques such as PET-CT and more tumor specific tracers will allow accurate delineation of the tumor spread. Accurate target definition and radiobiological response information is paramount for radiobiological based treatment planning and precise dose delivery. Advanced treatment monitoring and verification methods for tumor response and dose delivery will assure maximum treatment quality when combined with biologically based treatment optimization. Also more dynamic properties of the treatment should be taken into account in the optimization process, such as organ motion, patient specific tumor responses during the cause of the treatment. Thus the therapeutic monitoring of the tumor by new dedicated image modalities such as PET-CT are important for the clinical outcome. High quality radiation therapy will in the future be based on sensitive tumor diagnostic such as PET-CT imaging. This will allow radiobiologically treatment optimized for high precision radiation therapy delivery and on-line treatment follow up using PET-CT therapeutic imaging for predictive assay based adaptive treatment optimization.

The BioArtist diagnostic therapy system is fully developed for clinical implementation of the BioArt concept. The system is a full integration of a therapy unit optimized for precise and high speed IMRT using narrow scanned photon beam with a diagnostic PET-CT tumor camera for in vivo therapeutic dose delivery imaging. Such a system will allow on-line treatment follow up of tumor spread, radiation sensitivity and in vivo dose delivery for adaptive treatment optimization. As this system utilizes narrow scanned photon beams, it will benefit from usage of the collimator of the invention. FIGS. 15 and 16 is a schematic overview of the BioArt treatment unit.

A new therapy strategy called BIO-ART, Biologically Optimised 3D-in vivo predictive Assay based Radiation Therapy is now being developed at the Karolinska Institutet, Sweden, and the Biocare consortium. The concept is based on PET-CT imaging of the tumor before radiation therapy and at early time during the actual IMRT-radiation therapy treatment to pick up the tumor responsiveness to the treatment and adaptively change the treatment to maximize the treatment outcome as illustrated in the figure. Initially, the patient is administered FDG (fluorodeoxyglucose) or more tumor specific tracers for PET-CT tumor imaging. The patient is treated for about 3-5 treatment fractions using biologically optimized intensity modulated therapy planning before a repeated PET-CT image is recorded to get tumor responsiveness data early on in the treatment after. About 3 to 5 treatment fractions later where still meaningful tumor imaging is feasible, the last PET-CT patient specific data set for the Predictive Assay of the tumor responsiveness is recorded to get a better knowledge of the influence of the rate of loss of functionality of the doomed tumor cells. A final revised treatment plan is made based on the tumor cell distribution and responsiveness image data sets. A high resolution and high sensitive PET-CT camera is developed also for integration in a therapy unit, a diagnostic therapy unit PET-CT-RT unit to allow simultaneously delineation of tumor spread as well as therapeutic imaging of the in vivo delivered dose distribution to exactly correlate the delivered dose to the tumor response in actual the treatment position.

This integrated PET-CT camera will allow in vivo dose delivery imaging of the patient in treatment position to be overlayed on the tumor cell density image and allow accurate dose delivery verification and treatment optimization based on actual 3D in vivo dose delivery and tumor responsiveness data.

The new diagnostic radiation therapy is designed for fast cost effective adaptive intensity modulated radiation therapy and is ideal for modern treatment protocols like BioArt:

The on-board high sensitivity and high resolution PET-CT camera will allow in vivo tumor diagnostics imaging for accurate delineation of the local and regional tumor spread and responsiveness as well as the delivered dose distribution.

The narrow high energy photon beams generates a very positron emitter activity by photonuclear reactions in the patient to allow accurate in vivo verification of the delivered dose distribution in 3D using the same high sensitivity PET-CT camera as used for the initial tumor diagnostics.

The total delivered dose distribution during fractionated radiation treatment can be optimally controlled by adaptation of the integrated dose delivery to the initial biologically optimized treatment plan tumor spread distribution, and the monitored tumor responsiveness to drastically increase both the quality and safety of the treatment, based on the BIO-ART strategy.

Fast pencil beam scanning technology offers a unique possibility to image the dose delivery and geometry of the whole patient volume in 3D using the relatively high pair production contrast by combined PET and radiotherapeutic-computed tomography.

The fast narrow photon and electron pencil beam scanning system integrated with a new ultra fast portal imager will allow improved patient set-up as well as dynamic dose delivery locking on a moving tumor in real time.

The beam scanning system can also be auto-calibrated and use real time dosimetric verification with a segmented high-resolution transmission monitor.

The irradiation time using narrow scanned beam is practically independent of the complexity of the desired dose distribution in contrast to IMRT-delivery using multileaf collimation where the treatment time is proportional to the complexity of the given fields.

Built in auto calibration system and remote check and confirm system.

Ergonomically designed treatment unit convenient to work around due to low height of tabletop.

The overall compact therapy unit size will save space in the treatment room.

For patients the systems described herein are offering a number of benefits, which implicitly translates into benefits for the clinic. These are:

Higher precision: Not only do Orbiter and BioArtist with their unique dual pivot couches [32] and solid stationary gantry designs offer a mechanically more stable treatment machine, but the built-in diagnostic and therapeutic imaging systems also allow for future biologically optimized adaptive treatment techniques.

Increased safety: With the inherent safe non-moving mechanical design any risk of collision is eliminated.

Ergonomic design: Both treatment units are compact and allowing close contact with the patient.

High patient throughput: The unique properties of the systems allow for up to 100% faster treatments, which is illustrated in FIGS. 15 and 16. FIG. 15 illustrates a comparison of treatment time (in minutes) for different radiation therapy systems and FIG. 16 illustrates a comparison of patient throughput (patients per hour) for different radiation therapy systems.

Low life cycle cost: The compact mechanical design of Orbiter and BioArtist will ensure high reliability and cost effective treatments.

Both systems are dedicated for modern treatment techniques like IMRT and adaptive radiation therapy but can also be used for conventional radiation therapy.

It will be understood by a person skilled in the art that various modifications and changes may be made to the present invention without departure from the scope thereof, which is defined by the appended claims.

REFERENCES

[1] European patent application no. 0 314 214
[2] B. Andreassen, "A fast and strong purging magnet for narrow scanned photon beams," M.Sc Thesis, Internal Report, Dept. of Medical Radiation Physics, Stockholm University, Sweden (2002).
[3] S. Larsson, "Radiation Transport Calculations for Narrow Scanned Photon Beams Using Geant4", M.Sc Thesis at Luleå University of Technology in Sweden, 2002:354 CIV, ISSN:1402-1617 (2002).
[4] R. Svensson, M. Åsell, P. Näfstadius and A. Brahme, "Target, purging magnet and electron collector design for scanned high-energy photon beams," Phys. Med. Biol. 43: 1091-1112 (1998).
[5] R. Svensson and A. Brahme, "Effective source size, yield and beam profile from multilayered bremsstrahlung targets" Phys. Med. Biol. 41: 1353-1379, (1996).
[6] A. Brahme, "On the optimal choice of scattering foils for electron therapy," TRITA-EPP-72-17 (1972).
[8] A. Brahme, "Design principles and clinical possibilities with a new generation of radiation therapy equipment," Acta Oncol. 26: 403-412 (1987).
[9] R. Svensson, "Development of a compact high energy treatment unit combining narrow pencil beam scanning and segmental multileaf collimation," Ph. D. thesis ISBN 91-7153-740-6 Stockholm University, Sweden (1998).
[10] S. O. Schriber and E. A. Heighway, IEEE Trans. Nucl. Sci., NS-22 No 3, 1060 (1975).
[11] S. Agostinelli et al, "GEANT 4—a simulation toolkit," Nucl. Instrum. Meth. Phys. Res A 506: 250-303 (2003).
[12] S. Larsson, R. Svensson, I. Gudowska, V. Ivanchenko and A. Brahme, "Radiation transport calculations for 50 MV photon therapy beam using the Monte Carlo code GEANT4," Radiat. Protect. Dosim. 115: 503-507 (2005).
[13] B. K. Lind "Properties of an algorithm for solving the inverse problem in radiation therapy," Inv. Probl. 6: 415-426 (1990).
[14] M. Karlsson, H. Nystrom and H. Svensson, "Photon beam characteristics on the MM50 racetrack microtron and a new approach for beam quality determination," Med. Phys. 20:143-149 (1993).
[15] M. Karlsson, H. Nystrom and H. Svensson, "Electron beam characteristics of the 50-MeV racetrack microtron", Med. Phys. 19: 307-315 (1992).
[16] A.-K. Ågren-Cronqvist, P. Källman and A. Brahme, "Determination of the relative seriality of a tissue from its response to non-uniform dose delivery," In: Modelling in Clinical Radiobiology, Ed. D. Baltas (1996).
[17] I. Lax and A. Brahme, "Collimation of high energy electron beams," Acta Radiol. Oncol. 19: 199-207 (1980).
[18] A. Brahme, "Electron transport phenomena and absorbed dose distributions in therapeutic electron beams," 14:th Int. Congr. Radiol. Rio de Janeiro, Brazil (1977).
[19] M. Hollmark, J. Uhrdin, D. Belkic, I. Gudowska and A. Brahme, "Influence of multiple scattering and energy loss straggling on the absorbed dose distributions of therapeutic light ion beams: I. Analytical pencil beam model," Phys. Med. Biol. 49: 3247-3265 (2004).
[20] ICRU Report 35, "Radiation Dosimetry: try: Electron beams with energies between 1 and 50 MeV" (1984).
[21] A. Gustafsson, B. K. Lind, R. Svensson and A. Brahme, "Simultaneous optimization of dynamic multileaf collimation and scanning patterns or compensation filters using a general pencil beam algorithm," Med. Phys. 22: 1141-1156 (1995).
[22] B. Lind and A. Brahme, "Optimization of radiation therapy dose distributions using scanned photon beams," Proc. 9:th Int. Conf. on Comp. in Rad. Therapy, Eds. Bruinvis IAD, Van der Giessen P H, Van Kleffens H J, Elsevier, Amsterdam, pp. 235-239 (1987).
[23] J. Löf, A. Liander, G. Kåver, B. K. Lind and A. Brahme, "ORBIT—A general object oriented code for radiotherapy optimization," Radiother. Oncol. 48 (suppl. 1): S69 (1998).
[24] R. Svensson, B. Lind and A. Brahme, "Beam characteristics and clinical possibilities of a new compact treatment unit design combining narrow pencil beam scanning and segmental multileaf collimation," Med. Phys. 25: 2358-2369 (1998).

[25] A. Brahme, "Treatment optimization using physical and biological objective functions," In: Radiation Therapy Physics, Ed.: Smith A., Berlin Springer, pp. 209-246 (1995).

[26] S. Söderström, A. Gustavsson and A. Brahme, "Few-field radiation therapy optimization in the phase space of complication free tumor control," Int. J. Imag. Syst. Technol. 6: 91-103 (1995).

[27] S. Söderström, and A. Brahme, "Which is the most suitable number of photon beam portals in coplanar radiation therapy?" Int. J. Radiat. Oncol. Biol. Phys. 33: 151-159 (1995).

[28] P. Aaltonen, A. Brahme, I. Lax, S. Levernes, I. Näslund, J. B. Reitan and I. Turesson, "Specification of dose delivery in radiation therapy. Recommendations by the Nordic Association of Clinical Physics (NACP)," Acta. Onc. 36 (suppl 10), ISSN 1100-1704 (1997).

[29] WO 00/74779

[30] WO 2004/000120

[31] WO 2007/021226

[32] WO 2004/028371

[33] A. Brahme, "Biologically optimized 3-dimensional in vivo predictive assay-based radiation therapy using positron emission tomography-computerized tomography imaging," Acta Onc. 42: 123-136 (2003).

The invention claimed is:

1. A radiation gantry comprising:
a radiation generator for generating an input radiation beam;
a radiation target;
a beam scanning system for directing and scanning said input radiation beam onto said radiation target to form a narrow scanned pencil radiation beam having full width of half maximum of no more than 32 mm;
a collimator for sharpening a penumbra of said narrow scanned pencil radiation beam, said collimator comprising at least one pair of collimator leaves, wherein:
a penumbra-trimming portion of a collimator leaf facing an opposite collimator leaf of a collimator leaf pair is made of a first metal or a first alloy of said first metal having a first linear radiation attenuation coefficient and said first metal has a first atomic number according to the periodic table of the elements, said penumbra-trimming portion having a thickness in a range of about 10 to 50 mm in the direction of said narrow scanned pencil radiation beam; and
a remaining support portion of said collimator leaf is made of a second metal or a second alloy of said second metal having a second linear radiation attenuation coefficient that is lower than said first linear radiation attenuation coefficient and said second metal has a second atomic number that is lower than said first atomic number.

2. The radiation gantry according to claim 1, wherein said radiation generator is arranged for providing an electron beam having an energy content of at least 50 MV.

3. The radiation gantry according to claim 1, wherein said radiation target has a thickness of about 2 to about 5 mm in the direction of said input radiation beam.

4. The radiation gantry according to claim 1, wherein said radiation target is made of a low atomic number material having an atomic number no larger than 40.

5. The radiation gantry according to claim 1, wherein said penumbra-trimming portion has a thickness in a range of about 15 to 30 mm in said direction of said narrow scanned pencil radiation beam.

6. The radiation gantry according to claim 5, wherein said penumbra-trimming portion has a thickness in a range of about 15 to 25 mm in said direction of said narrow scanned pencil radiation beam.

7. The radiation gantry according to claim 1, wherein said narrow scanned pencil radiation beam has full width of half maximum of not more than 16 mm.

8. The radiation gantry according to claim 1, wherein said collimator comprises multiple adjacent pairs of collimator leaves and wherein:
a first side of said collimator leaf facing a first neighboring collimator leaf comprises a longitudinal shoulder adapted for running in a longitudinal groove of said first neighboring collimator leaf; and
a second opposite side of said collimator leaf facing a second neighboring collimator leaf comprises a longitudinal groove adapted for engaging a longitudinal shoulder of said second neighboring collimator leaf.

9. The radiation gantry according to claim 1, wherein said first metal or said first alloy of said first metal is selected from tungsten, osmium and iridium or an alloy of at least one of tungsten, osmium and iridium.

10. The radiation gantry according to claim 1, wherein said second metal or said second alloy of said second metal is selected from steel and aluminum.

11. The radiation gantry according to claim 1, wherein an upper portion of said penumbra-trimming portion extends a first distance into said collimator leaf and a lower portion of said penumbra-trimming portion extends a second distance into said collimator leaf, said second distance being shorter than said first distance.

12. The radiation gantry according to claim 1, wherein an end side of said penumbra-trimming portion facing said opposite collimator leaf comprises a groove designed for engagement with a shoulder protruding from a penumbra trimming portion of said another collimator leaf.

13. The radiation gantry according to claim 1, wherein an end side of said penumbra-trimming portion facing said opposite collimator leaf comprises a shoulder designed for running in an adapted groove of a penumbra-trimming portion of said another collimator leaf.

14. The radiation gantry according to claim 1, further comprising a purging magnet positioned immediately downstream of said radiation target but upstream of said collimator for deflecting a portion of said input radiation beam transmitted through said radiation target into a collector.

15. A method of sharpening the penumbra of a radiation beam comprising:
generating an input radiation beam;
directing and scanning said input radiation beam onto a radiation target to form a narrow scanned pencil radiation beam having full width of half maximum of no more than 32 mm;
sharpening a penumbra of said narrow scanned pencil radiation beam by a collimator comprising at least one pair of collimator leaves, wherein:
a penumbra-trimming portion of a collimator leaf facing an opposite collimator leaf of a collimator leaf pair is made of a first metal or a first alloy of said first metal having a first linear radiation attenuation coefficient and said first metal has a first atomic number according to the periodic table of the elements, said penumbra-trimming portion having a thickness in a range of about 10 to 50 mm in the direction of said narrow scanned pencil radiation beam; and a remaining support portion of said collimator leaf is made of a second metal or a second alloy of said second metal having a second linear radiation attenuation coefficient that is lower than said first linear radiation attenuation coefficient and said second metal has a second atomic number that is lower than said first atomic number.

16. A radiation gantry comprising:

a radiation generator for generating an input radiation beam;

a radiation target;

a beam scanning system for directing and scanning said input radiation beam onto said radiation target to form a narrow scanned pencil radiation beam;

a collimator for sharpening a penumbra of said narrow scanned pencil radiation beam, said collimator comprising at least one pair of collimator leaves, wherein:

a penumbra-trimming portion of a collimator leaf facing an opposite collimator leaf of a collimator leaf pair is made of a first metal or a first alloy of said first metal having a first linear radiation attenuation coefficient and said first metal has a first atomic number according to the periodic table of the elements, said penumbra-trimming portion having a thickness in a range of about 10 to 50 mm in the direction of said narrow scanned pencil radiation beam; and a remaining support portion of said collimator leaf is made of a second metal or a second alloy of said second metal having a second linear radiation attenuation coefficient that is lower than said first linear radiation attenuation coefficient and said second metal has a second atomic number that is lower than said first atomic number.

* * * * *